US012559725B2

(12) United States Patent
Yang et al.

(10) Patent No.: US 12,559,725 B2
(45) Date of Patent: Feb. 24, 2026

(54) FORMULATION COMPRISING EXTRACELLULAR VESICLES, METHOD FOR PRODUCING THE SAME, AND USES THEREOF

(71) Applicant: MacKay Memorial Hospital, Taipei (TW)

(72) Inventors: Kuen-Der Yang, Taichung (TW); Yeou-Ping Tsao, Taipei (TW); Chie-Pein Chen, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 718 days.

(21) Appl. No.: 16/702,560

(22) Filed: Dec. 4, 2019

(65) Prior Publication Data

US 2020/0095553 A1     Mar. 26, 2020

Related U.S. Application Data

(62) Division of application No. 16/018,055, filed on Jun. 26, 2018, now Pat. No. 11,692,172.

(51) Int. Cl.

| | |
|---|---|
| *C12N 5/0775* | (2010.01) |
| *A61K 9/50* | (2006.01) |
| *A61K 31/713* | (2006.01) |
| *A61K 35/28* | (2015.01) |
| *A61K 38/17* | (2006.01) |
| *A61K 41/10* | (2020.01) |
| *A61K 41/17* | (2020.01) |
| *A61P 9/00* | (2006.01) |
| *A61P 29/00* | (2006.01) |
| *A61P 35/00* | (2006.01) |
| *C12N 5/073* | (2010.01) |
| *C12N 15/11* | (2006.01) |
| *C12N 15/113* | (2010.01) |

(52) U.S. Cl.
CPC .............. *C12N 5/0665* (2013.01); *A61K 9/50* (2013.01); *A61K 9/5068* (2013.01); *A61K 31/713* (2013.01); *A61K 35/28* (2013.01); *A61K 38/179* (2013.01); *A61K 41/10* (2020.01); *A61K 41/17* (2020.01); *C12N 5/0605* (2013.01); *C12N 15/111* (2013.01); *C12N 15/113* (2013.01); *A61P 9/00* (2018.01);

*A61P 29/00* (2018.01); *A61P 35/00* (2018.01); *C12N 2310/141* (2013.01); *C12N 2320/32* (2013.01); *C12N 2500/02* (2013.01); *C12N 2500/30* (2013.01); *C12N 2501/65* (2013.01)

(58) Field of Classification Search
CPC ................ A61K 31/713; A61K 38/179; A61K 41/0009; A61K 9/50; A61K 9/5068; C12N 15/111; C12N 15/113; C12N 2310/141; C12N 2320/32; C12N 2501/65; C12N 5/0605; C12N 5/0665
USPC ........................................................ 424/450
See application file for complete search history.

(56) References Cited

U.S. PATENT DOCUMENTS

| | | | | |
|---|---|---|---|---|
| 9,433,645 B2 * | 9/2016 | Ra | .......................... | C12N 5/0667 |
| 2012/0315324 A1 * | 12/2012 | Zhang | .................. | A61K 31/353 |
| | | | | 514/274 |
| 2019/0093105 A1 * | 3/2019 | Gibbings | ............. | A61K 9/0019 |

FOREIGN PATENT DOCUMENTS

| | | | | |
|---|---|---|---|---|
| WO | WO-2012125471 A1 * | 9/2012 | ........... | A61K 31/573 |
| WO | WO-2013172793 A1 * | 11/2013 | ............. | A61K 35/28 |

OTHER PUBLICATIONS

Sun et al. Mol Ther. Sep. 2010;18(9):1606-14 (Year: 2010).*
Sun et al. Mol Ther. Sep. 2010; 18(9):1606-14. doi: 10.1038/mt. 2010.105. Epub Jun. 22, 2010. (Year: 2010).*

* cited by examiner

*Primary Examiner* — Fereydoun G Sajjadi
*Assistant Examiner* — Joel D Levin
(74) *Attorney, Agent, or Firm* — Sughrue Mion, PLLC

(57) ABSTRACT

Disclosed herein is a formulation comprising an extracellular vesicle (EV), and a therapeutic active agent induced or embedded in the EV. According to preferred embodiments of the present disclosure, the EV is isolated from umbilical cord mesenchymal stem cells, and the active agent may be a growth factor, an immune-modulating agent, a small molecule, an siRNA, cDNA or a plant ingredient; for example, curcumin. Also disclosed herein are methods for producing the present formulation, and uses of the present formulation in the treatment of various diseases.

3 Claims, 18 Drawing Sheets
(6 of 18 Drawing Sheet(s) Filed in Color)

Specification includes a Sequence Listing.

(C)

(D)

(C)

(D)

(A)

(B)

(A)

Control        Vehicle        EV        EV-curcumin (B)

(A)

(B)

(A)

(B)

Dorsal root ganglion (DRG) of L5          Dorsal root ganglion (DRG) of L4

SEQUENCE LISTING

<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: synthesized

<400> SEQUENCE: 1

-continued

Ser Ile Tyr Arg Arg Gly Ala Arg Arg Trp Arg Lys Leu
1               5                   10

<210> SEQ ID NO 2
<211> LENGTH: 23
<212> TYPE: RNA
<213> ORGANISM: Artificial Sequence
<220> FEATURE:
<223> OTHER INFORMATION: synthesized

<400> SEQUENCE: 2
cacaaauucg gaucuacagg gua                                                    23

FORMULATION COMPRISING EXTRACELLULAR VESICLES, METHOD FOR PRODUCING THE SAME, AND USES THEREOF

CROSS-REFERENCE TO RELATED APPLICATIONS

This application is a divisional application of U.S. application Ser. No. 16/018,055, filed Jun. 26, 2018, which claims the benefit of U.S. Provisional Application No. 62/524,624, filed Jun. 26, 2017; the content of the application is incorporated herein by reference in its entirety.

BACKGROUND OF THE INVENTION

1. Field of the Invention

The present disclosure in general relates to the field of a biological delivery system. More particularly, the present disclosure relates to an extracellular vesicle (EV) formulation comprising one or more active agents, and the uses thereof.

2. Description of Related Art

Extracellular vesicle (EV) is a cell-derived membrane vesicle, and represents an endogenous mechanism for intercellular communication. In general, a cell (i.e., a donor cell) may release different types of EVs, including exosome (with diameter ranging from 50 to 150 nm), and microvesicle (with diameter ranging from 50 nm to 500 nm). The released EVs can be up-taken by a recipient cell via endocytosis, membrane fusion or specific ligand-receptor internalization, and thereby resulted in delivering the content of EVs (e.g., the nucleic acid, lipopolysaccharide, protein and/or lipid from the donor cell) to the recipient cells.

EVs can be isolated from various sources of biofluids, such as blood, urine, cerebrospinal fluid, malignant ascites, breast milk, bronchoalveolar lavage and saliva. Since the content of EVs reflects the status of the donor cell, it may be used as a biomarker in the application of diagnosis, prognosis, and epidemiology. For example, EVs derived from cancer cells or released from nearby stromal cells or leukocytes may be released into circulation for guiding cancer cell invasion and metastasis; vice versa, mesenchymal stem cells and/or immune cells may release EVs in response to cancer cells for antagonism of cancer cell invasion and metastasis. Accordingly, the EVs isolated from ascites is useful for diagnosing ovarian cancer and determining the stage of the diseases; whereas the EVs isolated from blood is useful for diagnosing ovarian cancer and breast cancer.

EV is also a suitable candidate for organelle therapy, based on the advantage of its lipid bilayer properties. EVs are capable of directing cell fusion, carrying proteins or miRNAs for cell-cell communications and even reaching distal organ such as kidney, lung and central nervous system via crossing the major biological membranes.

EV is also a suitable candidate for drug delivery, based on the advantage of high biocompatible, low immunogenicity, nanoparticle size, and capable of crossing the major biological barriers (including blood-brain barrier (BBB)). However, the therapeutic effect usually varies with the factors, such as disease, disease severity and the EV property (e.g., the cellular origin, the size and the content of EVs). Formulations of EVs with pre-conditional culture stimulations, or with post-isolation incorporation of small molecules, peptides, nucleic acids, aptamers or scaffolds may improve and expand the therapeutic applications.

In view of the foregoing, there exists in the related art a need for a modified EV that can be wildly applied in the treatment of various diseases, such as inflammatory disease, degenerative disease, infectious disease, metabolic disease, dysplastic disease, diabetes and cancer.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

One aspect of the present disclosure is directed to a formulation, which comprises an EV and one or more active agent encapsulated in the EV. According to embodiments of the present disclosure, the EV is derived from a mesenchymal stem cell. Preferably, the mesenchymal stem cell is isolated from Wharton jelly of umbilical cord.

The active agent is selected from the group consisting of, a growth factor, an immune-modulating agent, an anti-cancer agent, an anti-inflammatory agent, an anti-infection agent, an anti-aging agent, an anti-oxidant agent, an anti-radiation agent, a nucleic acid and a combination thereof. According to some embodiments of the present disclosure, the active agent is aspirin, bryostatin or curcumin. According to other embodiments, the active agent is the nucleic acid selected from the group consisting of, small interference ribonucleic acid (siRNA), small hairpin ribonucleic acid (shRNA), and micro-ribonucleic acid (miRNA). According to alternative embodiments of the present disclosure, the active agent is a polypeptide, which modulates T cell differentiation. Additionally or alternatively, the active agent may be an anti-oxidant agent, a biological agent, or an anti-aging agent such as metformin, β-lapachone etc.

According to certain embodiments, the present formulation is prepared by a method comprising the steps of, (a-1) isolating the EV from the mesenchymal stem cell; and (b-1) mixing the isolated EV of step (a-1) and the active agent so as to encapsulate the active agent in the isolated EV.

Alternatively, the present formulation is prepared by a method comprising the steps of, (a-2) subjecting the mesenchymal stem cell to the treatment of the active agent; and (b-2) isolating the EV from the active agent treated mesenchymal stem cell of step (a-2).

Still alternatively, the present formulation is prepared by a method comprising the steps of, (a-3) irradiating the mesenchymal stem cell with a linear accelerator, X-ray or gamma ray; and (b-3) isolating the EV from the irradiated mesenchymal stem cell of step (a-3).

According to some embodiments of the present disclosure, in the step (a), the mesenchymal stem cell is irradiated with X-ray at a dose of 1-10 Gray (Gy). More preferably, the mesenchymal stem cell is irradiated with X-ray at a dose of 1-5 Gy. According to one working example, the mesenchymal stem cell is irradiated with X-ray at a dose of 3 Gy.

Another aspect of the present disclosure pertains to a method of treating an inflammatory disease, dry eye, degenerative disease, cancer, infectious disease and/or aging in a subject. The method comprises administering to the subject an effective amount of the present formulation.

Non-limiting examples of the inflammatory diseases include psoriasis, colitis, burn injury, acute kidney injury, traumatic brain injury, skin injury, arthritis and autoimmune diseases.

The degenerative diseases treatable with the present method include, but are not limited to, Parkinson's disease, Alzheimer's disease, dementia, stroke, chronic kidney disease, chronic lung disease and hearing loss.

The cancer treatable with the present method may be any of gastric cancer, lung cancer, bladder cancer, breast cancer, pancreatic cancer, renal cancer, colorectal cancer, cervical cancer, ovarian cancer, brain tumor, prostate cancer, hepatocellular carcinoma, melanoma, esophageal carcinoma, multiple myeloma, or head and neck squamous cell carcinoma.

Regarding the infectious disease, it may be caused by a bacterium, virus or fungus.

In general, the formulation disclosed herein may be administered to the subject by a suitable route. Non-limiting examples of the suitable route include, topical, mucosal (e.g. intraconjunctival, intranasal, intratracheal), oral, intraspinal (e.g. intrathecal), intravenous, intraarterial, intramuscular, subcutaneous, intraarticular, intraventrical, intracerebroventricular, intraperitoneal injection and intra-middle ear administration.

The subject is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DETAILED DESCRIPTION OF THE INVENTION

Figure 1:
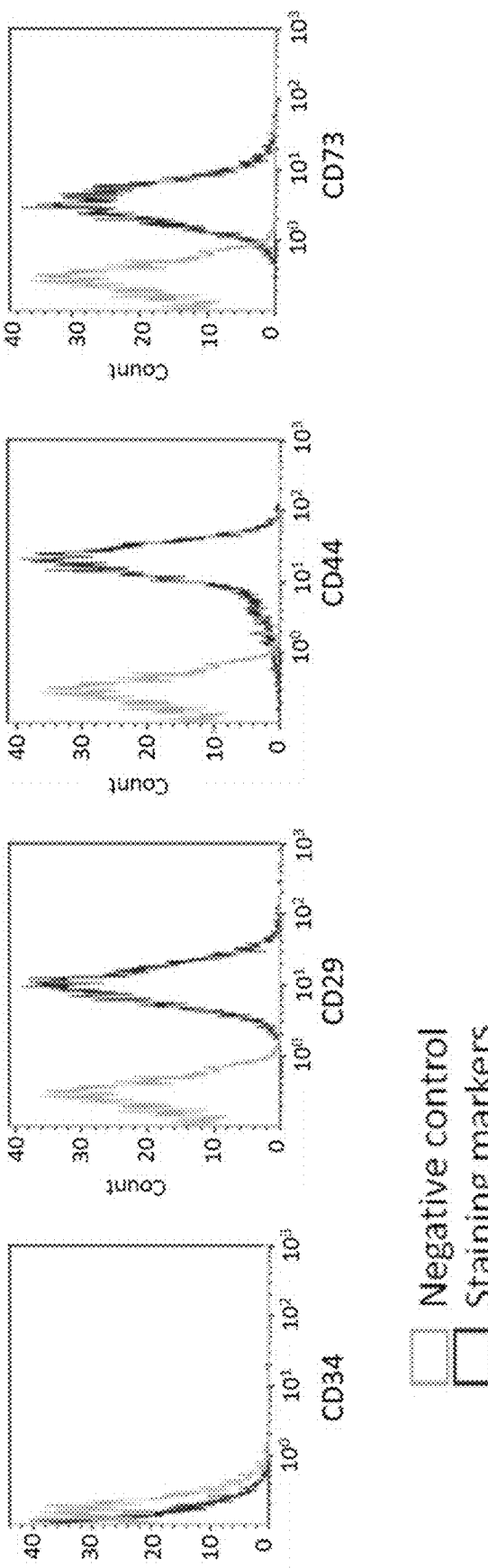
FIG. 1 is the data of flow cytometry that depicts the expression of cellular marker on umbilical cord mesenchymal stem cells (ucMSCs) according to one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "formulation" as used herein refers to an composition including one or more phospholipids, and one or more active agents encapsulated or embedded by said one or more phospholipids. The formulation of the present disclosure comprises an EV, which has the structure of a liposome (i.e., a hydrophilic core enclosed by a lipid bilayer), and at least one active agent encapsulated in the liposome structure of EV.

The term "encapsulate" refers to the process of encompassing, encasing, or otherwise associating two or more materials such that the encapsulated material is immobilized within or onto the encapsulating material. The term "encapsulate" as used herein refers to the inclusion of one or more molecule (e.g., the present active agent) in a hollow particle, for example, in the hydrophilic core of EV. In general, the active agent may be surrounded or partially surrounded by the lipid bilayer of EV.

As used herein, the term "Wharton's jelly", also known as inter-laminar jelly, is a subset of the umbilical cord matrix, and refers to a mucous-connective tissue substance found in the umbilical cord. The components of Wharton's Jelly include a mucous connective tissue, which comprises myo-fibroblasts, fibroblasts, macrophages, mesenchymal stem cells and an amorphous ground substance composed of hyaluronic acid and possibly other as yet uncharacterized cell populations. Wharton's Jelly is one component of the umbilical cord.

The term "effective amount" as referred to herein designate the quantity of a component, which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the formulation of the present disclosure), such as molar concentration, mass concentration, volume concentration, molality, mole fraction, mass fraction and mixing ratio. Specifically, the term "therapeutically effective amount" used in connection with the formulation described herein refers to the quantity of the formulation, which is sufficient to alleviate or ameliorate the symptoms associated with the inflammatory disease, degenerative disease, infectious disease, metabolic disease, dysplastic disease, diabetes or cancer in the subject. Persons having ordinary skills could calculate the human equivalent dose (HED) for the medicament (such as the present formulation) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to a mammal including the human species that is treatable with methods of the present invention. The term "subject" is intended to refer to both the male and female gender unless one gender is specifically indicated.

II. DESCRIPTION OF THE INVENTION

The objective of the present disclosure aims at providing a formulation comprising an EV and one or more active agent, methods of producing the formulation, the uses thereof.

(I) The Present Formulation

The first aspect of the present disclosure is directed to a formulation, which comprises an EV derived from a mesenchymal stem cell (MSC), which, in term, is isolated from Wharton jelly; and one or more active agent encapsulated therein.

EV is a spherical vesicle having the structure of a liposome, i.e., a hydrophilic core enclosed by a lipid bilayer; thus is suitable as a means for drug delivery, in which active agent(s) may be encapsulated in the liposome structure. Depending on desired effects, the active agent suitable for encapsulating in the EV liposome structure may be any of a growth factor, an immune-modulating agent, an anti-cancer agent, an anti-inflammatory agent, an anti-infection agent, an anti-aging agent, an anti-oxidant agent, an anti-radiation agent, a vitamin, a heat-shock protein (HSP), a nucleic acid, a plant ingredient, or a combination thereof.

Compared with the EV derived from other tissues/cells, the EV derived from umbilical cord mesenchymal stem cells (ucMSCs) is advantageous in at least the five following aspects:

(1) Similar to umbilical cord blood, in which different factors derived from stem cells or serum have been shown to rescue animals with aging. The EVs isolated from ucMSCs comprise higher levels of growth factors, including placental growth factor (PLGF) and granulocyte colony-stimulating factor (G-CSF).

(2) According to proteomic analysis, the expression level of proliferative molecules is higher in ucMSCs than in adult type MSCs.

(3) Compared with adult type MSCs, ucMSCs possess longer telomeres. The proliferation capability renders ucMSCs suitable for large-scale preparation of EVs.

(4) EVs derived from ucMSCs can be treated with irradiation or modulators so as to prepare desired formulations for the treatment of regenerative, anti-infectious or anti-inflammatory disorders, or produce a radio-protecting effect.

(5) EVs possess lipid bilayer property, which can be loaded with peptides or nucleic acids, such as DNA aptamers, RNA aptamers, miRNA, siRNA and etc.

(6) The EVs may be prepared as an anti-alkaline, anti-acid, or anti-freeze formulation via integrating desired compounds (e.g., the hydrophobic or hydrophilic compound) in the liposome structure thereof.

According to certain embodiments of the present disclosure, the active agent is a plant ingredient extracted from a plant component selected from the group consisting of leaf, stalk, root, flower, tuber, pollen, fruit and seed. Alternatively, the active agent may be an ingredient extracted from a fungus or bacteria. According to certain examples, the active agent is aspirin, lipopolysaccharide, quercetin, curcumin, astragalus, resveratrol, astaxathin or polyphenol. In one working example of the present disclosure, the active agent is curcumin.

According to some embodiments of the present disclosure, the active agent is the growth factor. Non-limiting examples of the growth factor include, but are not limited to, angiopoietin, macrophage colony-stimulating factor (M-CSF), granulocyte colony-stimulating factor (G-CSF), granulocyte macrophage colony-stimulating factor (GM- CSF), placental growth factor (PLGF), vascular endothelial growth factor (VEGF), fibroblast growth factor (FGF), epidermal growth factor (EGF), one morphogenetic protein (BMP), endoglin, endothelin, leptin, follistatin, hepatocyte growth factor (HGF), insulin-like growth factor (IGF), keratinocyte growth factor (KGF), nerve growth factor (NGF), growth factor-α (TGF-α), transforming growth factor-β (TGF-β), cartilage growth factor (CGF), stem cell factor (SCF), brain-derived neurotrophic factor (BDNF), platelet-derived growth factor (PDGF), interleukin (IL) and ephrin. In one working example of the present disclosure, the active agents are angiopoietin, endoglin, FGF-2, HGF, IL-8 and VEGF-C.

Exemplary anti-cancer drugs include, but are not limited to, curcumin, interferons, cytokines (e.g., tumor necrosis factor, interferon α, interferon γ), antibodies (e.g. Herceptin (trastuzumab), T-DM1, AVASTIN (bevacizumab), ERBITUX (cetuximab), Vectibix (panitumumab), Rituxan (rituximab), and Bexxar (tositumomab)), anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin A analogs, Vitamin D3 analogs (e.g. EB 1089, CB 1093, and KH 1060), vitamin K, isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca²⁺ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Examples of anti-inflammatory molecule include, but are not limited to curcumin, non-steroidal anti-inflammatory drugs (NSAIDs) including, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluoromethalone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium. In addition, cytokine antagonists, such as aptamers of IL-10, IL-6, IL-8, TNF-alpha (TNF-α), IL-5, IL-13, TGF-beta (TGF-β), VEGF and etc., may be used for anti-inflammatory effects.

Non-limiting examples of anti-oxidant agents include amine (e.g., N,N-diethylhydroxylamine, and amino-guanidine), arginine pilolate, ascorbic acid and its salts, ascorbyl ester of fatty acid, bioflavonoid, butylated hydroxy benzoic acid and its salt, dihydroxy fumaric acid and its salts, gallic acid and its alkyl esters (e.g., propyl gallate, and uric acid), glycine pidolate, 6-hydroxy-2,5,7,8-tetramethylchroman-2-carboxylic acid, lipoic acid, lysine, melanin, methionine, nordihydroguaiaretic acid, proline, silymarin, sorbic acid and its salts, sulfhydryl compounds (e.g., glutathione), superoxide dismutase, catalase, tea extract, grape skin/seed extract, rosemary extract, tocopherol acetate, tocopherol, tocopherol sorbate and the combination thereof. These incorporations can be loaded into a scaffold for better tissue localization.

Examples of anti-aging agent include, but are not limited to, curcumin, coenzyme Q10, xanthophyll (e.g., astaxanthin, fucoxanthin and zeaxanthin), L-glutathione, retinoid, α-hydroxyl acids, β-hydroxyl acid and lutein. Alternatively, the anti-aging agent may be a proteoglycan, a glycoprotein or a glycolipid, which is optionally loaded into a scaffold for better tissue localization.

Examples of anti-infectious agent include, but are not limited to, LL37, interferon alpha, hydrophilic and hydrophobic antibiotics, and aptamers.

The vitamin is any of vitamin A, vitamin D, vitamin K or vitamin E.

Non-limiting examples of HSP include, but are not limited to, HSP10, HSP27, HSP40, HSP60, HSP70, HSP72, HSP90, HSP100 and HSP104.

The nucleic acid may be a DNA or RNA. According to certain embodiments of the present disclosure, the nucleic acid is an RNA, for example, an siRNA, an shRNA or an miRNA. Alternatively, the nucleic acid may be a DNA aptamer, an RNA aptamer, or an affixmer. Non-limiting examples of the miRNA include agomirs (such as miRNA125a, miRNA21, miRNA214, miRNA410, miRNA495 and 548L-5p etc.), and antagomirs (such as miRNA10a, miRNA182-5p, miRNA155a etc.). In one working example of the present disclosure, the nucleic acid is miRNA10a, which comprises the nucleotide sequence of SEQ ID NO: 2.

Alternatively, the active agent of the present formulation may be an asta-carotenoid selected from the group consisting of, astaxanthin, carotene, echinenone, canthaxanthin, adonirubin, doradexanthin, zeaxanthin, antheraxanthin, violaxanthin, neoxanthin and a combination thereof.

Non-limiting examples of immune-modulating agent include, interleukin (such as IL-2, IL-7, IL-12), cytokine (such as granulocyte colony-stimulating factor (G-CSF) and interferon (IFN)), chemokine (such as CXCL13, CCL26 and CXCL7), antagonist of immune checkpoint (such as anti-CTLA-4, anti-PD1 or anti-PD-L1 (ligand of PD-1), anti- LAG3, anti-B7-H3, synthetic cytosine phosphate-guanosine (CpG) oligodeoxynucleotide, and glucan), and modulator of Tregs (such as cyclophosphamide). In one specific example of the present disclosure, the immune-modulating agent is a polypeptide comprising the amino acid sequence of SEQ ID NO: 1.

In some embodiments, the active agent is aspirin, lipopolysaccharide, metformin, peptides or bryostatin.

The produced formulation is stable to freeze condition (e.g., being stable for at least three months in liquid or freeze dried form), acid treatment (e.g., the formulation comprising astaxathin), and alkaline treatment (e.g., the formulation comprising curcumin). In addition, the present formulation is also stable in polyols, such as glycerol and polyethylene glycol (PEG).

(II) Production of the Present Formulation

The active agent may be incorporated into the liposome structure of EVs via a pre-conditional treatment (e.g., incubating the active agent with the MSCs, or treating the MSCs with an irradiation or a small molecule such as aspirin, metformin, lipopolysaccharide, or resveratrol) or a post-isolation treatment (e.g., incorporating the active agent such as astaxathin or curcumin, with EVs derived from MSCs treated with or without irradiation). The present disclosure provides three exemplary methods for the preparation the present EV formulation.

The first method comprises the steps of, (a-1) isolating EVs from a mesenchymal stem cell (MSC); and (b-1) mixing the isolated EVs of step (a-1) and an active agent so as to encapsulating the active agent therein.

In general, EVs may be isolated from suitable sources, preferably, from MSCs in accordance with process well known in the related art. Examples of method suitable for such purpose include, but are not limited to, differential centrifugation, sucrose gradient centrifugation, microfiltration, antibody-coated magnetic bead, bioreactor and microfluidic device. Alternatively, EVs may be isolated from tissues/biofluids with the aid of suitable commercial kit, such as, EXOQUICK.

According to embodiments of the present disclosure, EVs are obtained from the culture supernatant of MSCs. Generally, MSCs are cultured in low glucose DMEM with 10% fetal bovine serum (FBS) followed by the treatment of a serum-free medium to induce the secretion of EVs from MSCs to the supernatant; the secreted EVs are then harvested by any suitable means. In one preferred embodiment, the secreted EVs in the supernatant are isolated by microfiltration, in which particles ranging from 0.02 to 0.20 μm are retained.

Alternatively, the hollow-fiber bioreactor (a three-dimensional cell culturing system) is used for the purpose of improving the EV production efficiency. The bioreactor is a compact system, in which a pump forces medium through a cartridge containing cell cultures (e.g., MSC cell culture), and tiny hollow fibers mediate the exchanges of nutrient and waste. The EVs produced by the cells (e.g., MSCs) secreting to the hollow fibers are captured in the medium and harvested by any suitable means.

To produce the present formulation, in the step (b-1), the isolated EVs of step (a-1) and active agents are mixed for sufficient periods of time or until the active agents are encapsulated in the liposome structure of each EVs. The excess amounts of active agents are then removed by centrifugation through a filter that cuts off at a size of about 20 nm, thereby producing the present EV formulation.

Optionally, depending on the nature of the active agent (i.e., hydrophobicity or hydrophilicity of the active agent), the amount of the active agent being loaded into the EVs may be improved by the use of sonication, electroporation, centrifugation, co-solvent, surfactant or lipid.

Alternatively, the present formulation may also be produced by a method comprising the steps of, (a-2) subjecting the mesenchymal stem cell to the treatment of the active agent or a polynucleotide encoding the active agent; and (b-2) isolating EVs from the active agent or the polynucleotide encoding the active agent treated mesenchymal stem cell of step (a-2).

In this embodiment, MSCs are cultured in a medium containing the active agent (e.g., metformin, lipopolysaccharide, bryostatin or aspirin) or the polypeptide useful in encoding the active agent for sufficient period of time, which allows EVs to be secreted into the supernatant, and subsequently being harvested therefrom. According to the embodiments of the present disclosure, the harvested EVs comprise the active surface proteoglycans, tetraspanins, peptides, growth factors and/or miRNAs therein.

According to certain embodiments, MSCs are cultured under pre-conditional incubation of active agent followed by the treatment of a hypoxic condition (e.g., 1% $O_2$) for 24-48 hours in a serum-free medium that promotes secretion of EVs, so that EVs released therefrom (i.e., from the cultured MSCs) would have comprised the active agent (e.g., proteoglycans, proteins, growth factors and/or miRNAs) on and/or inside the lipid bilayer vesicles.

In the case when the active agent is a peptide (protein) or a RNA (miRNA or siRNA), the peptide/protein aptamers or nucleic acids (e.g. DNA aptamers, RNA aptamers, lipid or glycan affixmers) can be incorporated into EVs harvested from MSCs, and alternatively, MSCs may be subject to transfection with a polynucleotide encoding such active agent, so that the active agent is expressed in the MSCs. The transfection can be done any method familiar to the skilled artisan; for example, calcium phosphate co-precipitation, electroporation, nucleofection, cell squeezing (gently squeezing the cell membrane), sonoporation (inducing pore formation in cell membrane by high-intensity ultrasound), optical transfection (generating a tiny hole in cell membrane by highly focused laser), impalefection (inserting into a cell DNA bound to the surface of a nanofiber), gene gun ("shooting" into the cell nucleus DNA coupled to a nanoparticle of an inert solid), magnetofection (using magnetic force to deliver DNA into target cells), viral transduction (using viruses as a carrier to deliver DNA into target cells), and transfection via a dendrimer, a liposome or a cationic polymer. After the transfected MSCs were cultured in a serum-free medium under a hypoxic condition for sufficient periods of time (e.g., 24-48 hours), the EVs secreted into the supernatant may then be harvested by similar methods described above.

Depending on the nature of the active agent to be loaded into the EV liposome, the encapsulation efficacy of the present formulation is about 10-90%, preferably about 30-70%, more preferably about 40-50%. According to one specific embodiment, 0.08 to 80 mM of curcumin are respectively mixed with 0.15 mg/ml EVs isolated from culture supernatants of $1.6 \times 10^{\ 7}$ cells/80 ml, and the encapsulation efficacy is about 46%-100% (0.01 mM: 46.2%, 0.2 mM: 100%, 1.0 mM: 100%).

Alternatively or optionally, the present formulation may be produced by a method comprising the steps of, (a-3) irradiating the mesenchymal stem cell with an electronic beam, an X-ray or a gamma ray; and (b-3) isolating EVs form the electronic beam, X-ray or gamma ray treated mesenchymal stem cell of step (a-3).

In this embodiment, MSCs are irradiated with a linear accelerator, an X-ray or a gamma ray, which induces MSCs to produce anti-inflammatory molecules, anti-aging molecules, anti-oxidation molecules and/or anti-radiation molecules. Accordingly, EVs secreted from irradiated MSCs would comprise any of the afore-mentioned molecules within their liposome structures. According to one specific embodiment, the MSCs are irradiated with X-ray at a dose of 1-10 Gy (e.g., 1, 2, 3, 4, 5, 6, 7, 8, 9, or 10 Gy), followed by the incubation under a hypoxic condition for 24-48 hours; the thus-produced EVs are then harvested. Preferably, the MSCs are irradiated with X-ray at a dose of 1-5 Gy. According to one working example of the present disclosure, the MSCs are irradiated with X-ray at a dose of 3 Gy.

The formulation produced by any of the methods mentioned above may serve as a biological delivery system, in which the liposome structure of each EVs acts as a reservoir to carry the active agent (e.g., plant ingredient, growth factor, anti-cancer drug, anti-inflammatory molecule, anti-aging molecule, anti-oxidant molecule, anti-irradiation molecule, anti-radiation molecule, vitamin, and/or asta-carotenoid) to a target cell, and as a shield to protect the active agent encapsulated therein from being rapidly degraded in the bloodstream. Once the present formulation is in contact with the target cell, the liposome structure of each EVs could then fuse with the cell membrane of the target cell, thereby releasing the encapsulated active agent in the target cell.

According to some embodiments of the present disclosure, the present formulation is about 20-200 nm in diameter.

According to optional embodiments of the present disclosure, the present formulation further comprises a helper molecule co-encapsulated or co-embedded in the liposome structure of each isolated EV so as to enhance the therapeutic effect of the active agent. The helper molecule and the active agent may be co-encapsulated or co-embedded into the EV liposome by use of co-solvent (e.g., PEG 400), surfactant (e.g., TWEEN-20) or lipid (e.g., LABRAFIL). Preferably, the helper molecule is a cytokine or a defensin.

The cytokine is selected from the group consisting of, granulocyte colony-stimulating factor (G-CSF), granulocyte macrophage colony-stimulating factor (GM-CSF), interleukin (IL; such as IL-1, IL-2, IL-5, IL-6, IL-8, IL-10, IL-11, IL-12, IL-13, IL-19, IL-20, IL-25, and IL-27), interferon (IFN; such as IFN-α, IFN-β, and IFN-γ), and tumor necrosis factor (TNF; such as TNFα and TNFβ). The defensin is α-defensin, β-defensin or θ-defensin.

According to embodiments of the present disclosure, the helper molecule and the active agent may be simultaneously or sequentially brought into contact with MSCs; thus, the EVs subsequently released from the MSCs would comprise both the helper molecule and the active agent in its structure. Depending on the nature of the helper molecule, suitable means is adopted to bring the helper molecule into contact with MSCs. For example, in the case when the helper molecule is the growth factor, cytokine, defensin or chaperone, it may be introduced into the MSCs via incubating the MSCs with a culture medium containing the helper molecule; on the other hand, if the helper molecule is a small molecule (e.g. aspirin or bryostatin), it is brought into contact with MSCs via its binding receptor or co-receptor and mediate immune regulation functions.

Alternatively, the helper molecule and the active agent may be simultaneously or sequentially loaded into an isolated EV via direct mixing, sonication, electroporation, centrifugation, gradient centrifugation, extrusion or the combination thereof, depending on the nature (e.g., hydrophobicity or hydrophilicity) of the helper molecule and the active agent.

As would be appreciated, the present formulation may be produced by bringing a first molecule into contact with MSCs via an appropriate method as described above, followed by mixing the EVs released therefrom (i.e., from the MSCs) with a second molecule via mixing, sonication, electroporation, centrifugation, gradient centrifugation, extrusion or the combination thereof. According to one embodiment, the first molecule is the helper molecule and the second molecule is the active agent. According to another embodiment, the first molecule is the active agent and the second molecule is the helper molecule.

(III) Use of the Present Formulation

The third aspect of the present disclosure is directed to the use of the present formulation according to any of the above-mentioned embodiments in treating various diseases, including inflammatory disease, dry eye, degenerative disease, cancer, infectious disease and aging.

According to the embodiments of the present disclosure, the method for treating a subject in need thereof comprises administering to the subject an effective amount of the present formulation. The present formulation may be administered via a route selected from the group consisting of, topical, mucosal (e.g. intraconjunctival, intranasal, intratracheal), oral, intraspinal (e.g. intrathecal), intravenous, intraarterial, intramuscular, subcutaneous, intraarticular, intraventrical, intracerebroventricular, intraperitoneal injection and intra-middle ear administration.

For the purpose of treating diseases, about $10^8$ to $10^{15}$ EVs (preferably, $10^9$ to $10^{14}$ EVs) of the present formulation, which give rise to about 0.1 μg to 1 g of the active agent, are administered to the subject. According to certain embodiments of the present disclosure, the subject is a mouse, in which about $10^{10}$ to $10^{13}$ EVs, which give rise to about 10 μg to 1 mg of the active agent, are sufficient to produce a therapeutic effect.

A skilled artisan could calculate the human equivalent dose (HED) of the present formulation, based on the doses determined from animal models. As would be appreciated, the actual dosage of the present EV formulation may be determined by the attending physician based on the physical and physiological factors of the subject, these factors include, but are not limited to, age, gender, body weight, body surface, the disease to be treated, severity of the condition, previous history, the presence of other medications, the route of administration and etc.

According to some embodiments, the present formulation is useful for treating a subject suffering from an inflammatory disease. The method comprises administering to the subject an effective amount of the present formulation to regulate the function or expression of immune cells, growth factors, chemokines and/or cytokines. Examples of inflammatory disease treatable by the present method include, but are not limited to, psoriasis, colitis, burn injury, acute kidney injury, traumatic brain injury, skin injury, arthritis and autoimmune diseases.

According to certain embodiments, the present formulation is useful for treating a subject suffering from a degenerative disease. The method comprises administering to the subject an effective amount of the present formulation to reduce oxidative stress in the subject. In one embodiment, the oxidative stress is reduced by suppressing the respiratory burst. In another embodiment, the oxidative stress is reduced by increasing the expression of growth factors. In still another embodiment, the oxidative stress is reduced by modulating the activation of AMP kinase. Non-limiting examples of degenerative disease treatable by the present method include Parkinson's disease, Alzheimer's disease, dementia, stroke, chronic kidney disease, chronic lung disease or hearing loss.

According to further embodiments, the present formulation is useful for treating a cancer in a subject. The method comprises administering to the subject an effective amount of the present formulation so as to inhibit cancer cell growth and/or inhibit cancer cell migration. Examples of the cancer that may be treated by the present method include, but are not limited to, gastric cancer, lung cancer, bladder cancer, breast cancer, pancreatic cancer, renal cancer, colorectal cancer, cervical cancer, ovarian cancer, brain tumor, prostate cancer, hepatocellular carcinoma, melanoma, esophageal carcinoma, multiple myeloma, and head and neck squamous cell carcinoma.

In certain embodiments of the present disclosure, the present formulation exhibits an anti-aging effect in the subject. According to one example, the present formulation improves the cognition ability in the subject.

According to alternative embodiments, the present formulation exhibit a therapeutic effect on spinal cord injury, in which the EV of the present formulation specifically targets the injured region of spinal cord.

Alternatively, the present formulation is useful in treating an infectious disease via promoting the direct microbicidal or immune defense (e.g. cell and humoral immunity) of the subject, in which the infection is caused by a bacterium, a virus or a fungus.

According to some working examples of the present disclosure, the active agent additively or synergistically enhances the therapeutic effect of EV. In certain examples, compared with the EV derived from cancer cells, the EV derived from ucMSCs provides a more efficient means to treat diseases.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Cell Culture

The C2C12 myoblasts were purchased from the Global Bioresource Center (ATCC), and cultured in Dulbecco modified eagle medium (DMEM) containing 10% FBS. The U937 myeloid cells and DLD-1 cancer cells purchased from ATCC were cultured in RPMI-1640 medium containing 10% FBS. All cells were incubated at 37° C. in a 5% $CO_2$ humidity incubator.

Isolation and Characterization of Umbilical Cord Mesenchymal Stem Cell (ucMSC)

A length of 5-cm umbilical cord was taken from an umbilical cord of normal spontaneous delivery. The 5-cm cord was put into a normal saline-containing conical tube and subject to harvest the matrix after stripping out the umbilical cord vessels. The umbilical cord matrix was cut into pieces about 1 cm in diameter and subject to the culture in a dish with low oxygen and low glucose DMEM. The ucMSCs (CD29$^+$, CD34$^-$, CD44$^+$ and CD73$^{-'}$) migrated from the umbilical cord matrix were confirmed by flow cytometry with specified antibodies. The analysis data was depicted in FIG. 1.

Isolation and Characterization of Extracellular Vesicles from ucMSC (Hereinafter ucMSC-Naive-EVs)

The ucMSCs were cultured in low glucose DMEM containing 10% FBS. To isolate the ucMSC-naive-EVs, the culture medium was replaced with the serum-free DMEM; after incubating under a normoxic or hypoxic condition for 48 hours, the supernatants were collected, and filtrated by a retention centrifugation (with a 0.02 um filter, the molecular weight cutoff value was about 100 kilodalton) and a 0.20 um filter. The ucMSC-naive-EVs having a diameter ranging between 0.02 to 0.20 um were isolated and concentrated (200× concentration). The concentrated ucMSC-naive-EVs were then analyzed by flow cytometry and western blotting with anti-CD81 and anti-CD63 antibodies, respectively.

Besides, the growth factors encapsulated in the ucMSC-naive-EV were analyzed by multiplex antibody-coated beads array. The data was summarized in Table 1.

Isolation of EVs Derived from Post-Isolation Incorporation

The hydrophobic curcumin (with cationic character) may be efficiently encapsulated in the liposome structure of EVs via incubation at room temperature and under a condition of pH 6.0-10.0. In the present study, 0, 0.02, 0.20 or 1.25 mM curcumin was added to 20 ml ucMSC-naive-EVs (about 1×10$^{11}$ vesicles/ml) in serum free medium (pH=10.0) followed by incubation at room temperature for 15 minutes. The mixture was then subject to a 0.02 μm filter so as to obtain the ucMSC-naive-EVs having curcumin encapsulated therein (hereinafter EV-curcumin; the final concentration was about 1.2 mg/ml). The incorporation efficacy of curcumin is 100% to 46.2%. The curcumin concentrations were measured by OD$_{420}$ nm and calculated by a standard curve made with a series of well-known concentrations.

Isolation of EVs Derived from Pre-Treated ucMSCs

Thirty culture dishes of ucMSCs, each dish with 4×10$^4$ cells/ml in 10 ml, were cultured in low glucose DMEM medium with 10% FBS and pre-treated with various small molecules, including aspirin (250 ng/ml) or bryostatin 1 (10 nM) for 1 day. The culture medium was replaced with serum-free low glucose DMEM medium 24 hours later, and the supernatant (300 ml) was collected and filtered by a 0.45 um filter to deplete cell debris, by another 0.2 um filter to cut-off apoptotic bodies, and finally by a cassette (cartridge) with 0.02 um filter to concentrate the EVs to 1.2 mg/ml so as to respectively obtain the aspirin-EV (7.1×10$^{12}$ vesicle/ml) and bryostatin-EV (2.7×10$^{12}$ vesicle/ml).

Isolation of EVs from a Linear Accelerator Irradiation Treated ucMSCs (Hereinafter ucMSC-Irradiation-EV)

ucMSCs (4×10$^4$ cells/ml in 300 ml) were cultured in low glucose DMEM medium with 10% FBS for 1 day. Then, the medium were replaced with the serum-free low glucose DMEM medium before the irradiation of 3 Gy (sublethal dose) delivered by a linear accelerator (Clinac 1800, Varian Associates, Inc., CA, USA). After the 3 Gy irradiation, the cells were cultured for another 2 days. The supernatant (300 ml) was collected and filtered in accordance with the protocols illustrated above.

For the purpose of evaluating the biological function of the thus-obtained ucMSC-irradiation-EVs, ucMSCs (3×10$^4$ cells/well) or C2C12 myoblasts (5×10$^4$ cells/ml) were cultured on a 48-well plate overnight. The serum-free media containing different ucMSC-irradiation-EVs were added to the cells followed by irradiating the cells with or without 6 Gy delivered by the linear accelerator in a single fraction. One day later, the reactive oxygen species (ROS) production was assessed by 1 μM dichlorofluorecein hydrochloride (DCFH) followed by the analysis of flow cytometry.

Incubation of EVs and Small Molecules

The polypeptide SIYRRGARRWRKL (also known as ZIP polypeptide, SEQ ID NO: 1, m.w. 1982.4, 0.5 uM) was mixed with 0.12 mg/ml ucMSC-naive-EVs (about (2.2×10$^{11}$ vesicle/ml) dissolved in RPMI medium followed by incubation at room temperature for 60 minutes. Compared with ucMSC-naive-EVs, the ucMSC-naive-EVs comprising the polypeptide (hereinafter EV-ZIP) exhibited higher molecular weight, and accordingly, may be isolated by filtration (the molecular weight cutoff value was about 100 kilodalton).

For the preparation of EVs having RNA (e.g., miRNA or siRNA) encapsulated therein, 100 ul of ucMSC-naive-EVs (about 10$^9$ vesicles, 100 ug) were incubated with 2 ug of miRNA-10a (CACAAAUUCGGAUCUACAGGGUA from 5'-end to 3'-end; SEQ ID NO: 2) in the transfection solution containing 10 ul transfection agent and 40 ul phosphate-buffered saline (PBS) buffer. The mixture was incubated at 37° C. for 10 minutes. The reaction was stopped by adding 30 ul stop solution (Exoquick) and left on 4° C. ice for 30 minutes. The ucMSC-naive-EVs comprising miRNA10a (hereinafter EV-miRNA10a) was separated with the ucMSC-naive-EVs via ultracentrifugation at 10,000 g for 5 minutes.

Treatment of Muscle Cells

C2C12 myoblasts (1×10$^3$ cells/well) were respectively administered with specified treatments under serum-free condition for 24 hours. The cell viability and proliferation of the treated C2C12 myoblasts were analyzed by trypan blue exclusion assay and CCK-8 cell proliferation assay.

Treatment of Myeloid Cells

The U937 myeloid cells were seeded in 24-well plate at a density of 8×10$^4$ cells/well (in 0.4 ml) followed by the stimulation of 100 nM PMA (phorbol myristate acetate) at 37° C., 5% CO2 incubator for 48 hours. The cells were washed with PBS twice before adding medium with and without ucMSC-naive-EVs (0.15 mg/ml), curcumin (Cur, 0.8 mM) or EV-curcumin (Cur/EVs, 0.8 mM) for 30 minutes. The reactions were incubated with DCFH (dichloro-fluorescein hydrochloride) at 1 uM for 20 minutes before flow cytometric analysis of H$_2$O$_2$-mediated fluorescence at 480 nm emission.

Analysis of miRNA Profiles in EVs

The EVs (1.0 ml, 2.2×10$^{12}$ vesicles/ml) harvested from DLD-1 cells (DEV) or ucMSCs (MEV), and the EVs having curcumin incorporated therein (EV-curcumin) were respectively subject to RNA extraction followed by miRNA sequencing analysis. In brief, 700 ul of QIAzol Lysis Reagent (Qiagen) was added to EV pellets for homogenation; the mixture was incubated at room temperature for 5 minutes, followed by adding 140 ul chloroform and vigorously shaking for 15 seconds. The RNA samples were harvested by 12,000 g at 4° C. for 15 minutes in accordance with the manufacturer's instruction. Small RNA sequencing (RNA-Seq), including microRNAs (miRNAs) sequencing was done by next generation sequencing (NGS). Small RNA-Seq can query thousands of miRNA sequences with unprecedented sensitivity and dynamic range using TRUSEQ® Small RNA (Illumina) sample preparation protocol. The data were matched to human short noncoding RNA sequences (*Homo sapiens* miRNAs, Hsa miR) and analyzed with miRBase database.

Analysis of Proteomic Profiles in EVs

The EVs (0.5 ml, $1.1 \times 10^{12}$ vesicles/ml) harvested from ucMSCs (MEV) or DLD-1 cells (DEV), and the EVs having curcumin incorporated therein (EV-curcumin) were respectively subject to a protein lysing buffer. The protein concentrations in different EVs were measured by protein assay kit, and equalized proteins from a mixture of 3 batches of samples were subjected to the ITRAQ™ (isobaric tags for relative and absolute quantification). The ITRAQ™ method is a protein quantitation method based on the peptides labelling with a compound that produces isobaric fragments. Employing Applied Biosystems ITRAQ™ Reagents (Applied Biosystems Inc., USA) provided as a set of four, isobaric (same mass) reagents: ITRAQ™ Reagent 114, ITRAQ™ Reagent 115, ITRAQ™ Reagent 116, and ITRAQ™ Reagent 117 to label the proteins of EVs, we made four reagents to allow 4-plex samples analysis in a LC/MS-MS experiment. A total of 1160 proteins was identified by this ITRAQ™. We define the comparison ratio over 2 and 4 as a cut-off to show the differential displays.

Effects of EVs on T Cell Differentiation

In response to stimulation, T cells differentiate from resting status (Tho) toward different directions of T cell functions. While the T cell differentiation into T helper 1 (Th1), T helper 2 (Th2), T regulatory (Treg) or Th17, their cell surface receptors express different characteristics. The CXCR3 expression presents Th1; the CCR4 expression presents Th2; CD25 expression presents Treg and CCR6 expression presents Th17 differentiation. Employing flow cytometric analyses of anti-CXCR3, anti-CCR4, anti-CD25 and anti-CCR6 antibodies (eBiosources Inc. USA), the T cell differentiation was analyzed by modulated with different EVs. In brief, peripheral blood mononuclear cells at 2×105 cells/well in 300 ul culture medium were incubated without or without anti-CD3 (10 ug/well) and anti-CD28 (2 ug/well) antibodies for 4 days; different EVs (including ucMSC-naive-EV, bryostatin-EV, aspirin-EV or EV-miRNA10a) was added into the well containing anti-CD3 and anti-CD28 antibodies on day 2 and day 3.

Skin Application of EVs to Treat Psoriasis

In a mouse psoriasis model, a formulation of 62.5 mg imiquimod (5%) in eye cream (187.5 mg) was used to induce mouse (BALB/c mice) psoriasis of ear auricles. The formulation was administered to the ear auricles of BALB/c mice for three consecutive days. Then, the mice were assigned into four groups: (A) control group, in which the formulation was administered to the ear auricles of mice from day 4 to day 7; (B) EV-treated group, in which the formulation containing $2 \times 10^{11}$ vesicles/mg of ucMSC-naive-EVs was administered to the ear auricles of mice from day 4 to day 7; (C) EV-curcumin group, in which the formulation containing $2 \times 10^{11}$ vesicles/mg (about 120 ug protein/mg) EV-curcumin was administered to the ear auricles of mice from day 4 to day 7; and (D) curcumin group, in which the formulation containing 1 uM curcumin was administered to the ear auricles of mice from day 4 to day 7. The morphology of ear auricle thickness and vessel inflammation (dilatation) were analyzed on day 14.

Mucosal Application of EVs to Treat Dry Eye

In a mouse model of dry eye, BALB/c mice were maintained at 23° C. under low humidity of 10% so as to induce the dry eye condition. The mice were also received escopan 0.15 ml (2.5 mg/ml) subcutaneously twice a day for 3 days. Three days after the mice (100%) developed dry eyes, the topical drop solution with or without ucMSC-naive-EVs or aspirin-EV at 10 ul (about 12 ug protein of EVs, $2.2 \times 10^{10}$ to $7.1 \times 10^{10}$ vesicles) was administered to the eyes of mice for 4 consecutive days. The conjunctival inflammation was evaluated by administration of 5 ul of 10% fluorescein for 30 seconds and washed with 1 ml PBS under anesthesia.

Parenteral Application of EVs to Treat Hearing Loss

In a mouse model of hearing loss, the inner cell damage was induced by administering to C57BL/6 mice 4 mg/kg cisplatin daily for 5 consecutive days, in which the mice were intraperitoneally treated with 0.1 ml PBS (serving as the negative control group), 0.1 ml ucMSC-naive-EVs or 0.1 ml EV-curcumin (about 120 ug protein of EVs, $2.2 \times 10^{11}$ to $2.8 \times 10^{11}$ vesicles) from day 1 to day 5. The protecting effect of ucMSC-naive-EVs and EV-curcumin was assessed by analyzing the cell number and function of the inner ear cells. To assess the protecting effect of the present EV formulation on hearing loss and inner ear cell death, auditory brain response (ABR) threshold at 12 kHz and immunofluorescence images of organ of Corti explants were measured 10 days post-treatment. To obtain the ucMSC-EVs preparations with and without curcumin incorporation enough for the animal study requiring a larger amount of EVs for daily intraperitoneal injection, the ucMSC-EVs in paired formulations with and without curcumin incorporation were prepared and stored at −80° C. for at least 3 months. To make sure homogeneous application of ucMSC-EV to each mouse, different batches of EVs were thawed and mixed for the experiment right before the animal study. One-way ANOVA with Duncan post hoc test was performed when compared with the control or cisplatin group.

Parenteral Application of EVs to Treating Aging Mice

In a mouse model of anti-aging, BALB/c mice were subcutaneously treated with 100 mg/kg D-galactose every day for 6 consecutive weeks. Then, the mice were intraperitoneally administered with 0.1 ml PBS (serving as the negative control group), 0.1 ml curcumin (1 µM), 0.1 ml ucMSC-naive-EVs, 0.1 ml EV-curcumin (about 120 ug protein of EVs, $2.2 \times 10^{11}$ vesicles), or 5 mg/kg β-lapachone three times a week for 3 weeks after 6 weeks of aging induction and the pre-test of cognition assessment. The anti-aging effect of ucMSC-naive-EVs and EV-curcumin was then assessed by the cognition ability in Morris water maze model.

Distribution of EVs in Spinal Cord

For the purpose of investigating the distribution of EVs in spinal cord, 1.2 mg/ml ($2.2 \times 10^{12}$ vesicles) of ucMSC-naive-EVs were intrathecally injected to Sprague-Dawley rats (n=3). In brief, the rats under-anesthesia were inserted with a catheter under intrathecal route for continuous infusion of ucMSC-naive-EVs at a rate of 1 ul per hour for 72 hours. The ucMSC-naive-EVs (400 ul) were labeled with 20 ul Exo-green protein labeling kit (Carboxyfluorescein Succinimidyl diacetate ester-CFSE, EXOG200A-1) at 37° C. for 10 minutes and stop at 4° C. for 30 minutes followed by centrifugation at 10,000 g for 5 minutes. The labeled ucMSC-naive-EVs were resuspended to 400 ul PBS for studies.

The rats with unilateral disruption of the dorsal root at L5 level were sacrificed, and the dorsal roots (including the un-injured L4 and injured L5 dorsal roots) thereof were harvested for tissue section and counter stained with DAPI (4′,6-diamidino-2-phenylindole). The distribution of ucMSC-naive-EVs in spinal cord was detected by a fluorescent microscope.

Example 1 Characterization of ucMSC-Naive-EVs

Figure 2:
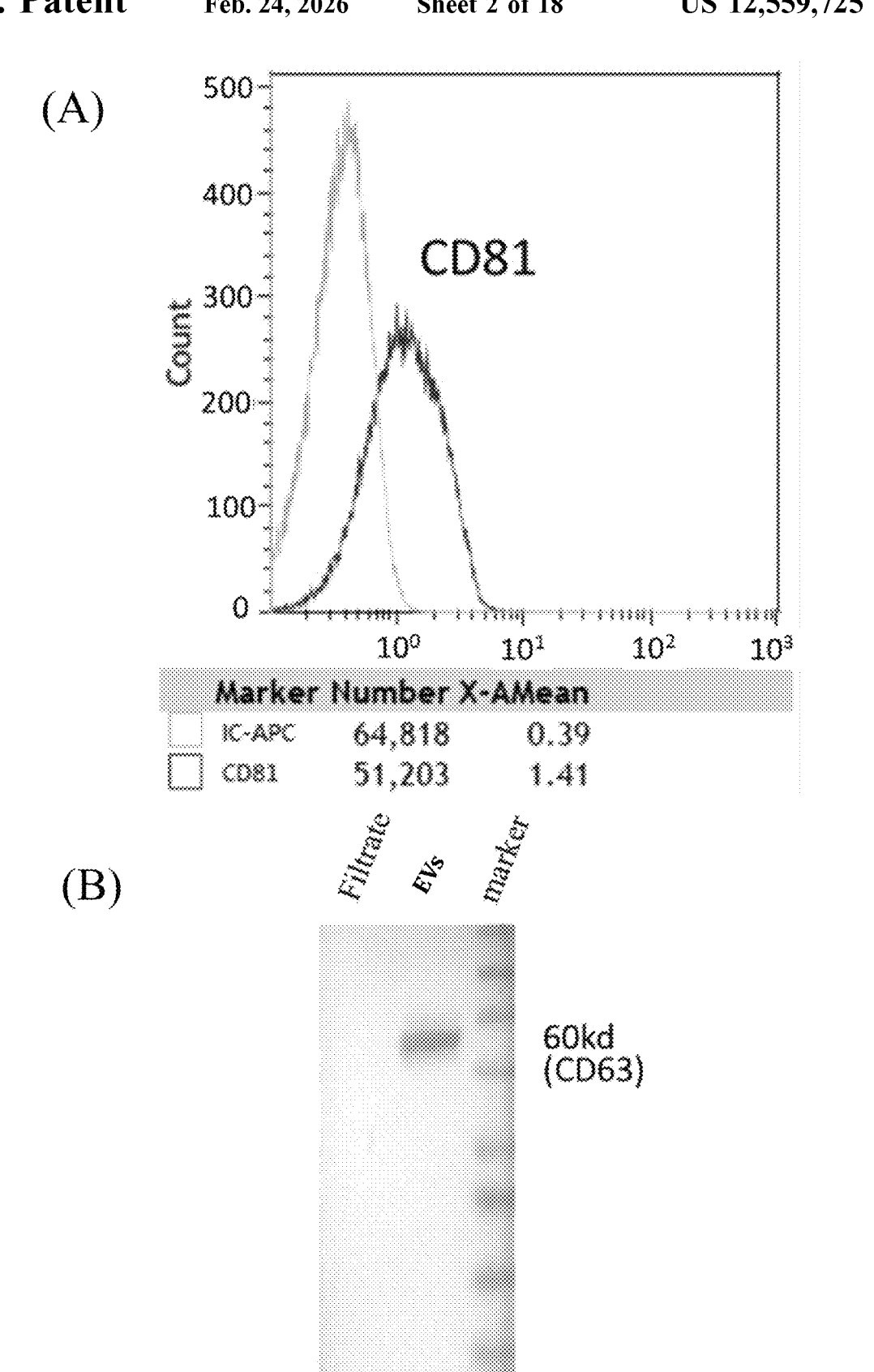
FIG. 2 is the data depicting the isolation and verification of ucMSC-naive-EVs (i.e., EVs derived from ucMSC without pre-treatment) according to Example 1 of the present disclosure. Panel A: the result of flow cytometry depicting the expression level of CD81 marker on ucMSC-naive-EVs. Panel B: the result of western blot depicting the expression level of CD63 marker on ucMSC-naive-EVs. Panel C: the result of transmission electron microscopy (TEM) depicting the morphology of ucMSC-naive-EVs, in which the diameter of ucMSC-naive-EVs was about 50-150 nm. Scale bar represents 0.1 um. Panel D: EVs promote the growth of C2C12 myoblasts in a dose-dependent manner, in which compared with the EVs derived from DLD-1 cancer cells (designated as DEV), the ucMSC-naive-EVs (designated as MEV) exhibited a significant effect on enhancing cellular growth.
Figure 2:
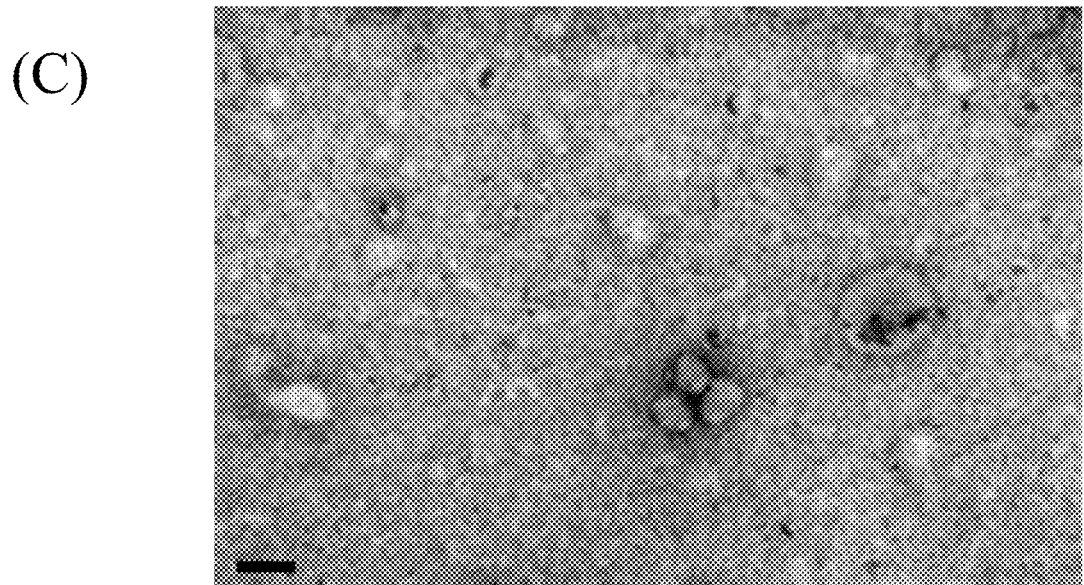
Figure 2:
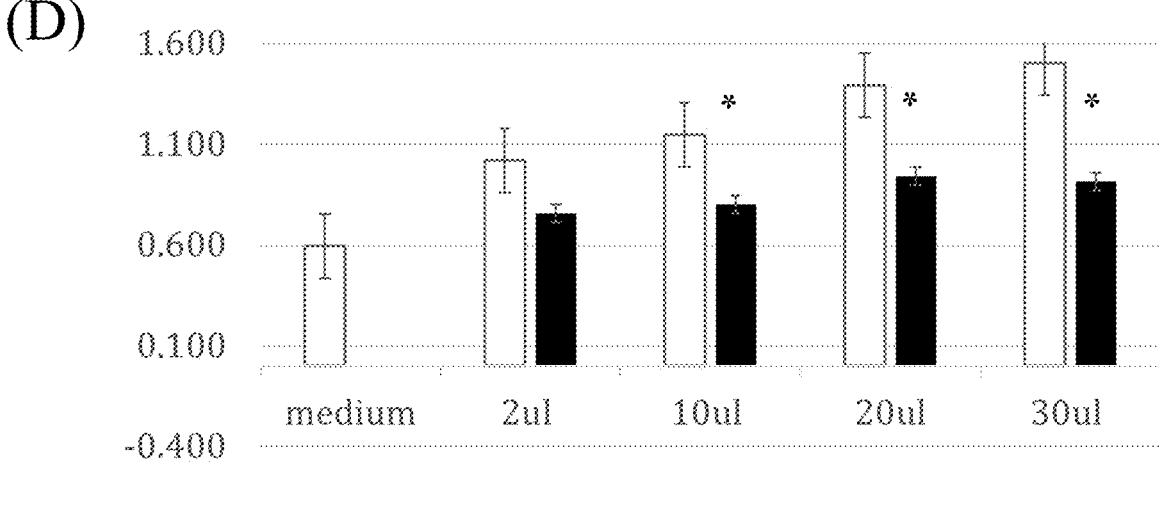

The bio-markers and bio-activity of ucMSC-naive-EVs were examined in this example, and the results were respectively depicted in Table 1 and FIG. 2.

The flow cytometry and western blotting analysis respectively demonstrated that the present ucMSC-naive-EVs exhibited both the tetraspanin CD81 and the EV marker CD63 (FIG. 2, Panel A and B). The size (50-150 nm) of the ucMSC-naive-EVs was further confirmed by TEM (FIG. 2, Panel C). The expression level of growth factors in ucMSC-naive-EVs was evaluated by multiplex antibody-coated beads array, and the results were summarized in Table 1.

TABLE 1

Growth factors in ucMSC-naive-EVs

| Growth factors | ucMSC-naive-EV | | | Drop through | | | |
|---|---|---|---|---|---|---|---|
| (pg/ml) | N | Mean | SE | N | Mean | SE | P values |
| Angiopoietin | 6 | 173.5 | 90.5 | 6 | 2.2 | 0.5 | 0.025 |
| Endoglin | 6 | 87.3 | 32.0 | 6 | 1.9 | 0.3 | 0.021 |
| FGF-2 | 6 | 57.2 | 9.7 | 6 | 31.9 | 0.7 | 0.021 |
| Follistatin | 6 | 6867.1 | 2404.7 | 6 | 143.8 | 56.4 | 0.011 |
| HGF | 6 | 11858.0 | 3141.4 | 6 | 48.1 | 16.7 | 0.011 |
| IL-8 | 6 | 99.2 | 40.6 | 6 | 31.4 | 17.9 | 0.033 |
| VEGF-C | 6 | 1353.0 | 185.7 | 6 | 77.7 | 24.4 | 0.001 |

The data of Table 1 indicated that various growth factors, including angiopoietin (a vascular growth factor regulating the angiogenesis pathway), endoglin (a subunit of the TGF-β receptor complex that regulates the angiogenesis and TGF-β signaling pathway), fibroblast growth factor-2 (FGF-2, also known as basic fibroblast growth factor; a growth factor possessing broad mitogenic and cell survival activities), follistatin (also known as activin-binding protein; a growth factor associated with cellular proliferation, inflammation, folliculogenesis, and development), hepatocyte growth factor (HGF, also known as scatter factor; a growth factor regulating cell growth, motility, morphogenesis, angiogenesis, tumorigenesis, tissue regeneration, and immune regulation), interleukin-8 (IL-8; a chemokine inducing chemotaxis of immune cells, and regulating immune response), vascular endothelial growth factor-C (VEGF-C; a member of the platelet-derived growth factor/vascular endothelial growth factor (PDGF/VEGF) family that plays a role in lymphangiogenesis, cellular survival, growth, migration, neural development, and blood pressure regulation) were encapsulated in ucMSC-naive-EVs.

For the purpose of investigating the bio-activity of EVs, the C2C12 myoblasts were treated with different doses of EVs isolated either from ucMSCs or from DLD-1 cancer cells. The data indicated that the treatment of EVs promoted cell growth in a dose-dependent manner (FIG. 2, Panel D). Further, compared with DLD-1-isolated EVs (designated as DEV), the EVs isolated from ucMSC (designated as MEV) significantly enhanced cell growth (P<0.01, n=6; FIG. 2, Panel D).

These results indicated that compared with the control group or EVs isolated from other cells, the present ucMSC-naive-EVs exhibited a more obvious effect on enhancing cell growth.

Example 2 Characterization of EVs Comprising Different Active Agents Therein 2.1 Bio-Activity In addition to ucMSC-naive-EVs, the bio-activity of EVs comprising curcumin (i.e., EV-curcumin) or miRNA10a (EV-miRNA10a), or the EVs isolated with pre-conditional treatment of bryostatin (i.e., bryostatin-EV) or aspirin (i.e., aspirin-EV) was measured in this example. The data were depicted in FIGS. 3-4, 7-8 and Table 2.

The expression level of growth factors in ucMSC-naive-EV and EV-curcumin were analyzed by multiplex antibody-coated beads array, and the results were summarized in Table 2.

TABLE 2

Growth factors in ucMSC-naive-EV and EV-curcumin

| Growth factors | ucMSC-naive-EV | | EV-Curcumin | | |
|---|---|---|---|---|---|
| (pg/ml) | Means | SE | Means | SE | P values |
| Angiopoietin | 452.1 | 476.3 | 402.1 | 161.2 | 0.171 |
| Endoglin | 169.6 | 101.2 | 114.1 | 37.9 | 0.500 |
| FGF-2 | 25.8 | 19.8 | 23.0 | 4.9 | 0.150 |
| Follistatin | 2993.8 | 1307.6 | 9999.8 | 2147.9 | 0.029 |
| HGF | 4148.8 | 2676.0 | 7224.6 | 837.1 | 0.242 |
| IL-8 | 173.5 | 141.8 | 2454.3 | 923.1 | 0.029 |
| VEGF-C | 1425.5 | 832.7 | 3230.8 | 302.2 | 0.100 |

Data presented are calculated from 4 experiments and tested by Mann Whitney U test.

The data of Table 2 indicated that compared to ucMSC-naive-EVs, the expression level of follistatin and IL-8 was significantly (p=0.029) higher in EV-curcumin, while the expression level of angiopoietin, endoglin, FGF-2, HGF and VEGF-C in EV-curcumin was similar with that of ucMSC-naive-EVs.

Figure 3:
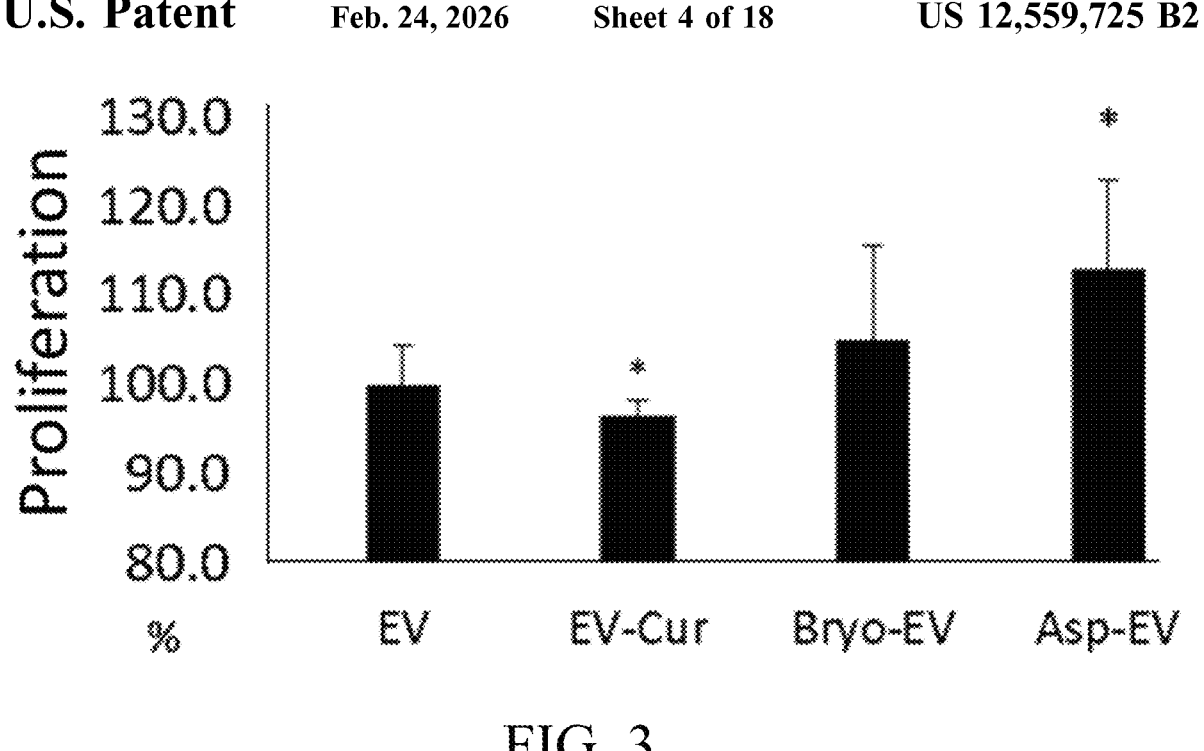
FIG. 3 is a histogram depicting the effect of specified EVs on the growth of muscle cell according to Example 2 of the present disclosure. EV: the C2C12 myoblasts treated with ucMSC-naive-EVs; EV-Cur: the C2C12 myoblasts treated with EV-curcumin (i.e., EV having curcumin encapsulated or embedded therein); Bryo-EV: the C2C12 myoblasts treated with bryostatin-EV (i.e., EV isolated from the culture supernatant of ucMSCs pretreated with bryostain for 24 hours); Asp-EV: the C2C12 myoblasts treated with aspirin-EV (i.e., EV isolated from the culture supernatant of ucMSCs pretreated with aspirin for 24 hours). * denotes $P<0.05$ as analyzed by Mann Whitney U test.

The data of FIG. 3 indicated that different EVs exhibited varied effects on the promotion of C2C12 cell growth, in which aspirin-EVs (Asp-EV) induced a significantly higher growth rate (P<0.05, n=3) than EV-Curcumin (EV-Cur).

Figure 4:
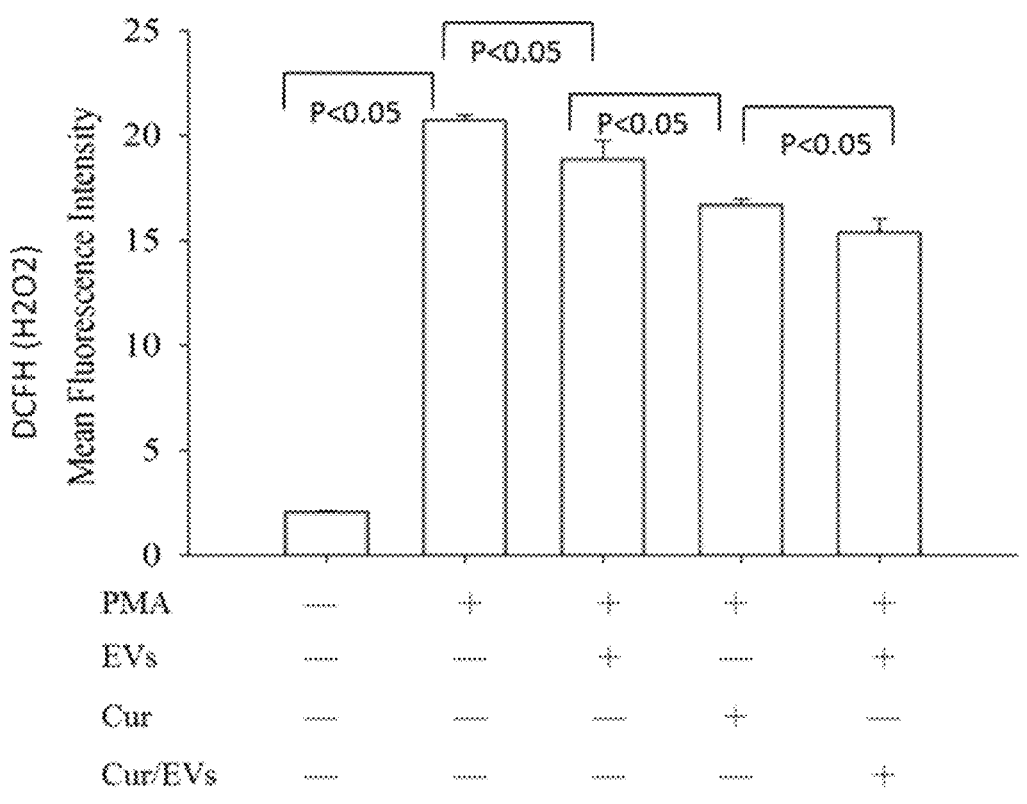
FIG. 4 is a histogram depicting the synergistic effect of specified treatment on anti-inflammation response according to Example 2 of the present disclosure, in which the EVs comprising curcumin therein (EV-Curcumin) significantly decreased the reactive oxygen species in cells. Data shown were calculated from 3 triplicate experiments and statistically analyzed by Mann Whitney U test.

For the purpose of investigating the effect on inflammatory response, U937 myeloid cells were respectively treated with medium only (serving as the negative control group), ucMSC-naive-EV (EVs), curcumin (Cur), and EV-curcumin (Cur/EVs). Compared with the control group, the treatment of ucMSC-naive-EV, curcumin or EV-curcumin significantly decreased the production of reactive oxygen species as determined by $H_2O_2$-mediated fluorescence at 480 nm emission, in which the incorporation of curcumin synergistically enhanced the anti-oxidation effect of ucMSC-naive-EV (FIG. 4).

Figure 8:
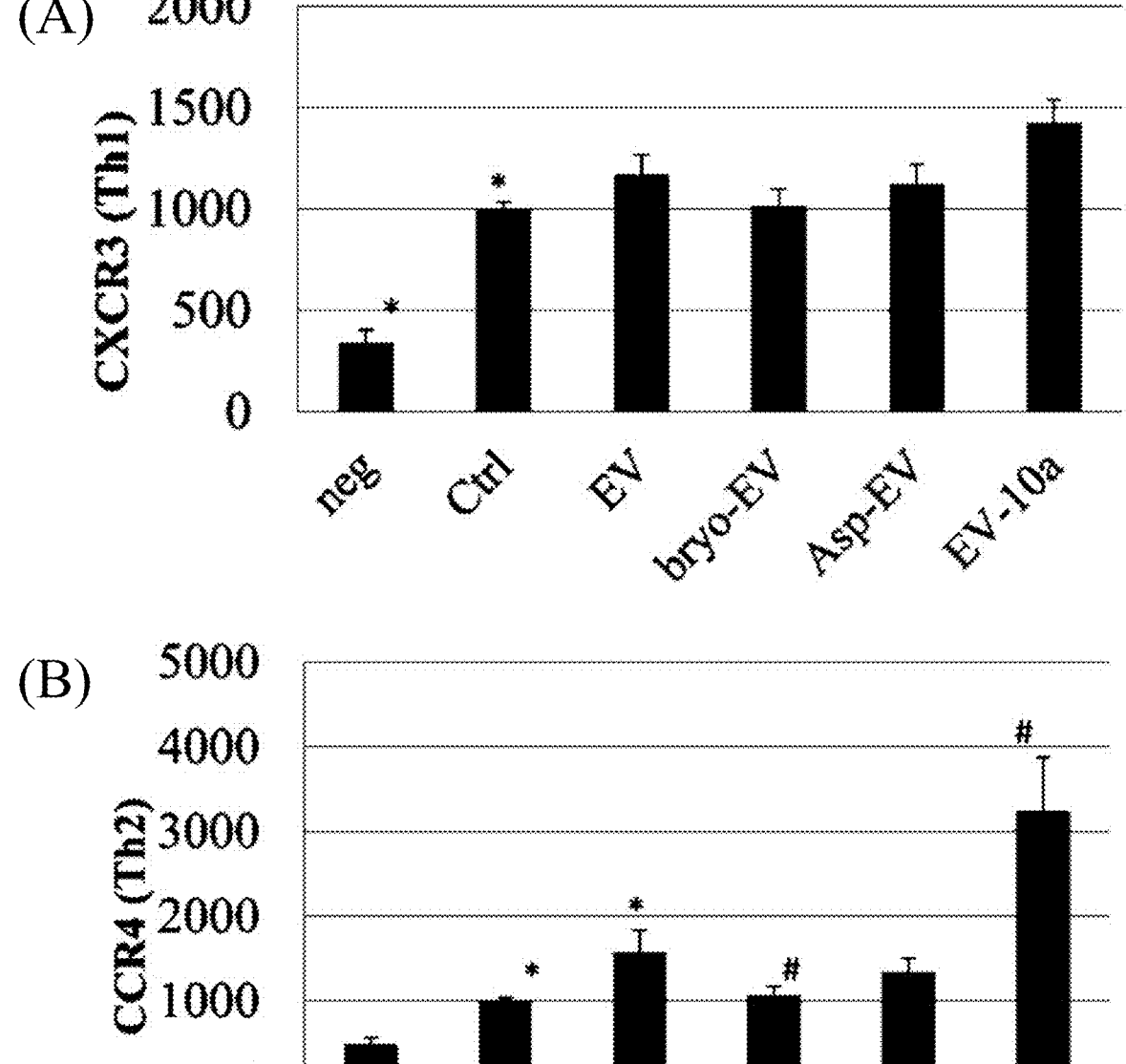
FIG. 8 is the data depicting the effect of specified EVs on regulating T cell differentiation according to Example 2 of the present disclosure. Panel A: the expression level of CXCR3, a cellular marker of Th1 cells; * denotes $P<0.05$ between neg group and Ctrl group. Panel B: the expression level of CCR4, a cellular marker of Th2 cells; * denotes $P<0.05$ between Ctrl group and EV group; # denotes $P<0.05$ between byro-EV group and EV-10a group. Panel C: the expression level of CD25, a cellular marker of regulatory T (Treg) cells; * denotes $P<0.05$ between Ctrl group and EV group; # denotes $P<0.05$ between byro-EV group and EV-10a group. Panel D: the expression level of CCR6, a cellular marker of Th17 cells; * denotes $P<0.05$ between byro-EV group and EV-10a group. neg: PBS treatment only; Ctrl: the treatment of anti-CD3 and anti-CD28 antibodies; EV: the treatment of anti-CD3 and anti-CD28 antibodies in the presence of ucMSC-naive-EV; byro-EV: the treatment of anti-CD3 and anti-CD28 antibodies in the presence of bryostatin-EV; Asp-EV: the treatment of anti-CD3 and anti-CD28 antibodies in the presence of aspirin-EV; EV-10a: the treatment of anti-CD3 and anti-CD28 antibodies in the presence of EV-miRNA10a (i.e., EV having miRNA10a encapsulated or embedded therein).
Figure 8:
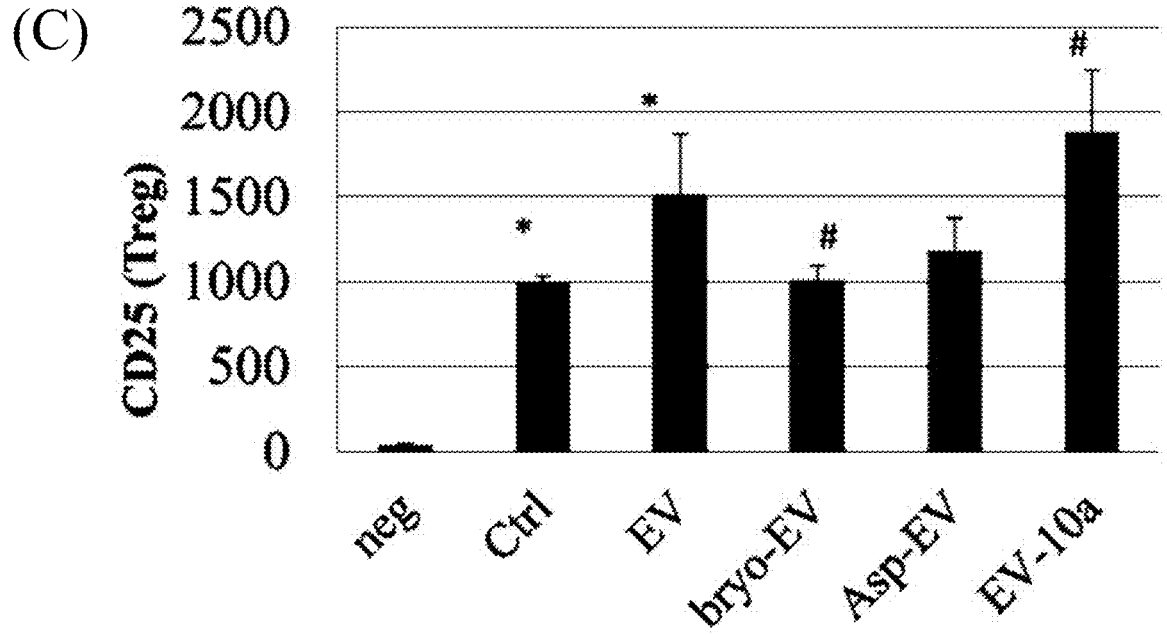
Figure 8:
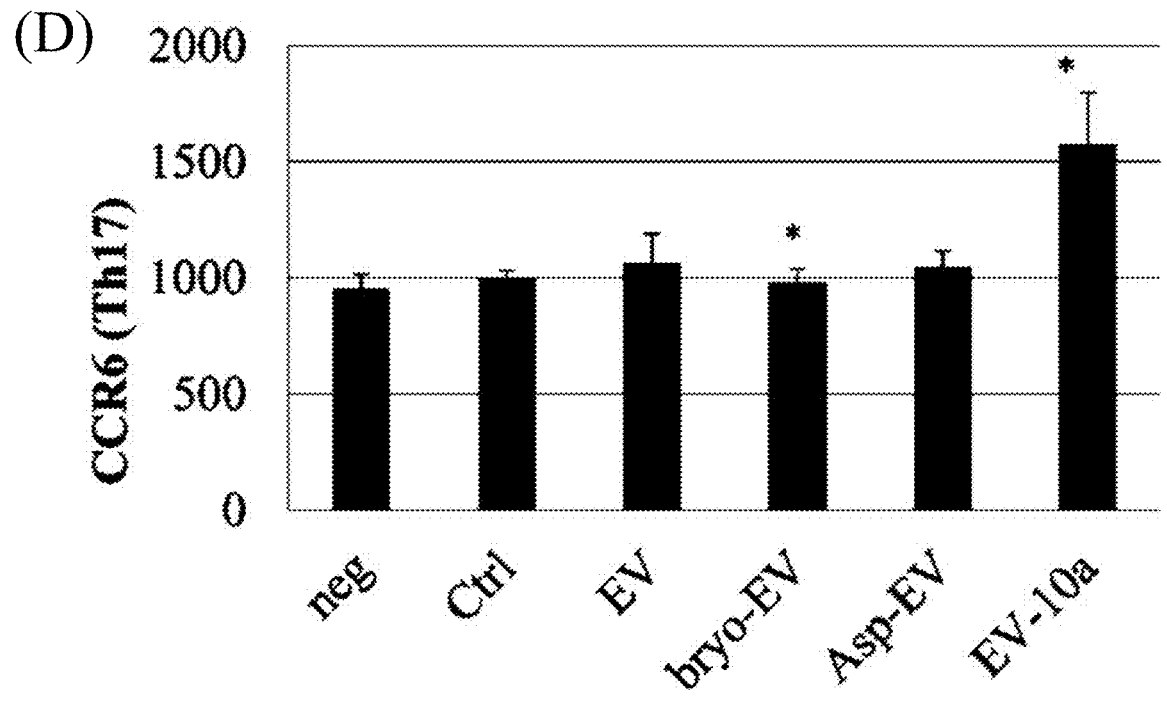

In addition, the effects of ucMSC-naive-EV, bryostatin-EV, aspirin-EV and EV-miRNA10a on T cell differentiation were also examined by flow cytometric analysis with antibody specific for CXCR3 (a marker of Th1 cells), CCR4 (a marker of Th2 cells), CD25 (a marker of Treg cells), or CCR6 (a marker of Th17 cells). Resting T cells had low level of differentiation marker expressed thereon, and the stimulation with anti-CD3 (10 ug/ml) and anti-CD28 (2 ug/ml) (Ctrl group) for 4 days significantly induced the expression of CXCR3, CCR4 and CD25 (P<0.01, n=6), but not the expression of CCR6 (FIG. 8). Additional administration of different EVs on day 2 and day 3 showed varied effects on the Th cell differentiation. The treatment of ucMSC-naive-EVs (EV) significantly enhanced CD25 and CCR4 expression (* denotes P<0.05, n=6); the data indicated that ucMSC-naive-EV (EV) treatment induced Treg and Th2 differentiation (FIG. 8, Panels B and C). On the other hand, compared with bryostatin-EV, the treatment of EV-miRNA10a significantly stimulated CCR4 (# denotes P<0.05, n=6) and CCR6 (* denotes P<0.05, n=6) expression by T (CD4) cells (FIG. 8, Panels B and D). All treatments did not obviously stimulated CXCR3 expression in comparison with the control group (FIG. 8, Panel A).

These results suggested that the active agent may additively or synergistically enhance the effect of ucMSC-naive-EVs on different types of cells and/or diseases.

2.2 Concentration and Size

The sizes and concentrations of different formulations of ucMSC-EVs comprising specified active agent were evaluated by NanoSight NS300 nanoparticle tracking analysis. The data of Table 3 and FIG. 7 indicated that the vesicles with sizes between 30 and 300 nm ranged between $2.2 \times 10^{12}$ and $7.1 \times 10^{12}$ vesicles/ml. The mean of vesicle sizes ranged between 151 and 175 nm, and the mode ranged between 107 and 174 nm (Table 3 and FIG. 7).

TABLE 3

| Number and size of different specified EVs | | | | |
|---|---|---|---|---|
| Number/Size | EV | EV-curcumin | bryostatin EV | aspirin-EV |
| Vesicles ($10^{12}$) | 2.18 | 2.79 | 2.73 | 7.08 |
| Mean (nm) | 162.3 | 151.2 | 167.2 | 175.4 |
| Mode (nm) | 143.2 | 106.7 | 174.1 | 165.6 |

Example 3 miRNA and Protein Expression in EVs

3.1 miRNA Expression

Figure 5:
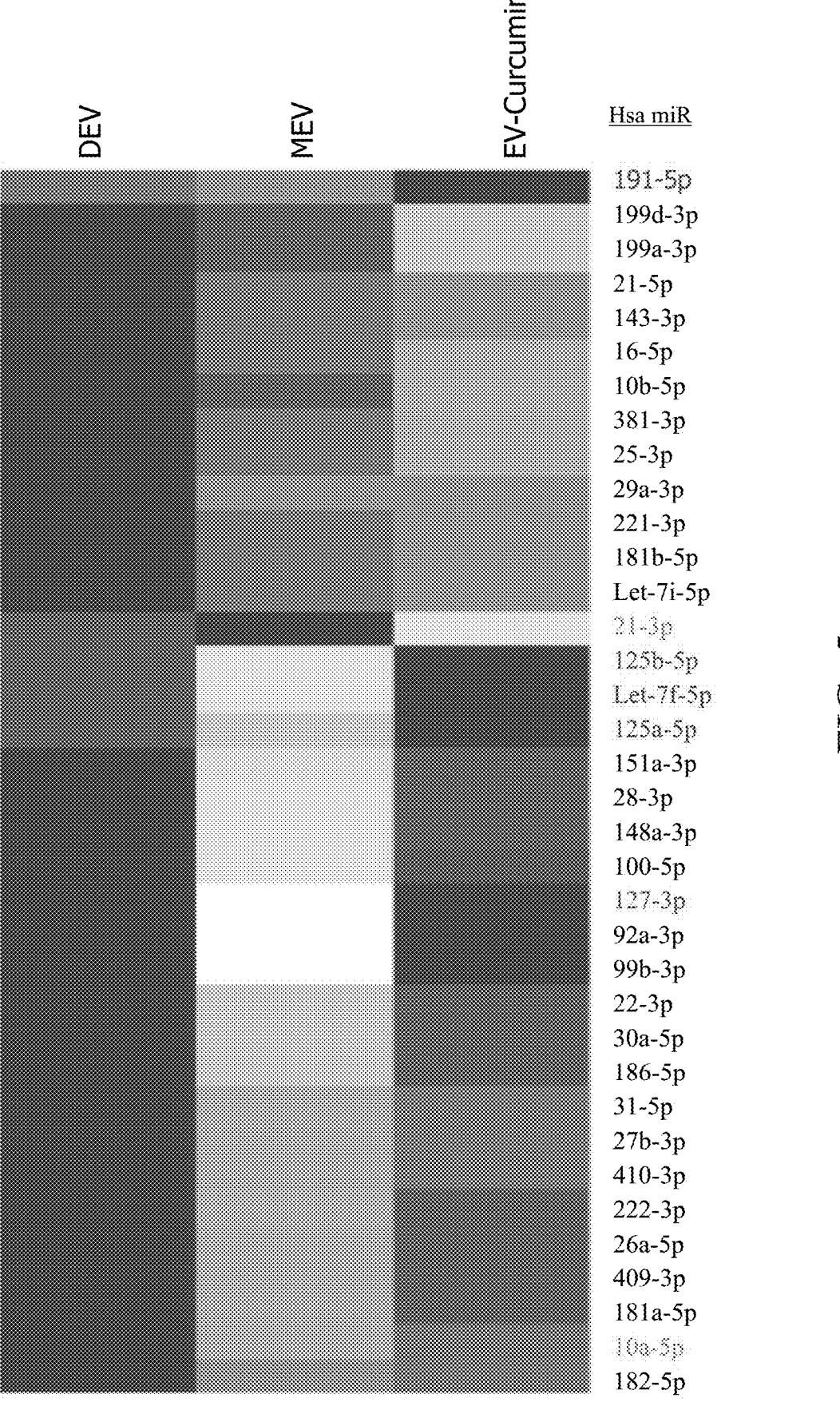
FIG. 5 is the data depicting the miRNA profiles of DLD-1-derived EVs (DEVs), ucMSC-naive-EVs (MEV), or EV-curcumin according to Example 3 of the present disclosure, in which 36 out of 2,000 *Homo sapiens* miRNAs (hsa miRs) were differently expressed in these EVs. Compared with ucMSC-naive-EV, the incorporation of curcumin increased the expression of 5 miRNAs (marked in red color) and decreased the expression of 2 miRNAs (marked in green color).

Based on over 2000 miRBase database, 36 Hsa miR were matched and identified, in which 2 miRNA (hsa miR10a-5p and miR182-5p) were overexpressed DLD-1-derived EVs (DEV), while the expression levels of the other 34 miRNAs were higher in ucMSC-naive-EV (MEV) with and without curcumin incorporation in comparison with the DLD-1-derived EVs (FIG. 5). As the data of FIG. 5 depicted, the miRNA profiles of ucMSC-naive-EVs were obviously different from that of DLD-1-derived EVs, in which the incorporation of curcumin increased the expression of 5 miRNAs (including 191-5p, 125b-5p, Let-7f-5p, 125a-5p and 127-3p), while decreased the expression of 2 miRNAs (including 10a-5p and 21-3p) in EVs.

3.2 Protein Expression

Figure 6:
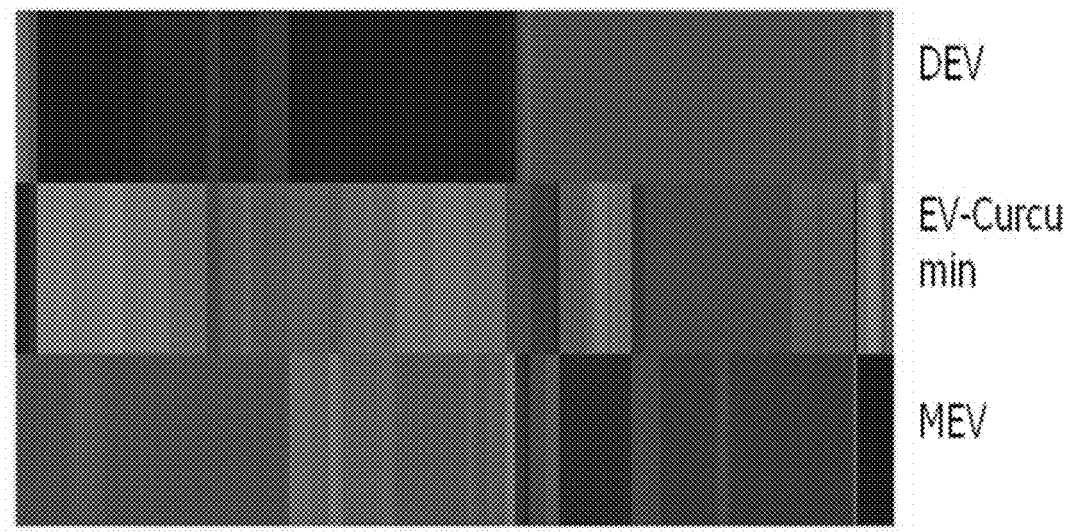
FIG. 6 is the data depicting the protein profiles of DLD-1-derived EVs (DEVs), ucMSC-naive-EVs (MEV), or EV-curcumin according to Example 3 of the present disclosure, in which the corporation of curcumin increased the expression of 6 proteins and decreased the expression of 4 proteins, while defining the increase over 4 fold and the decrease under 1/4 fold.
Figure 7:
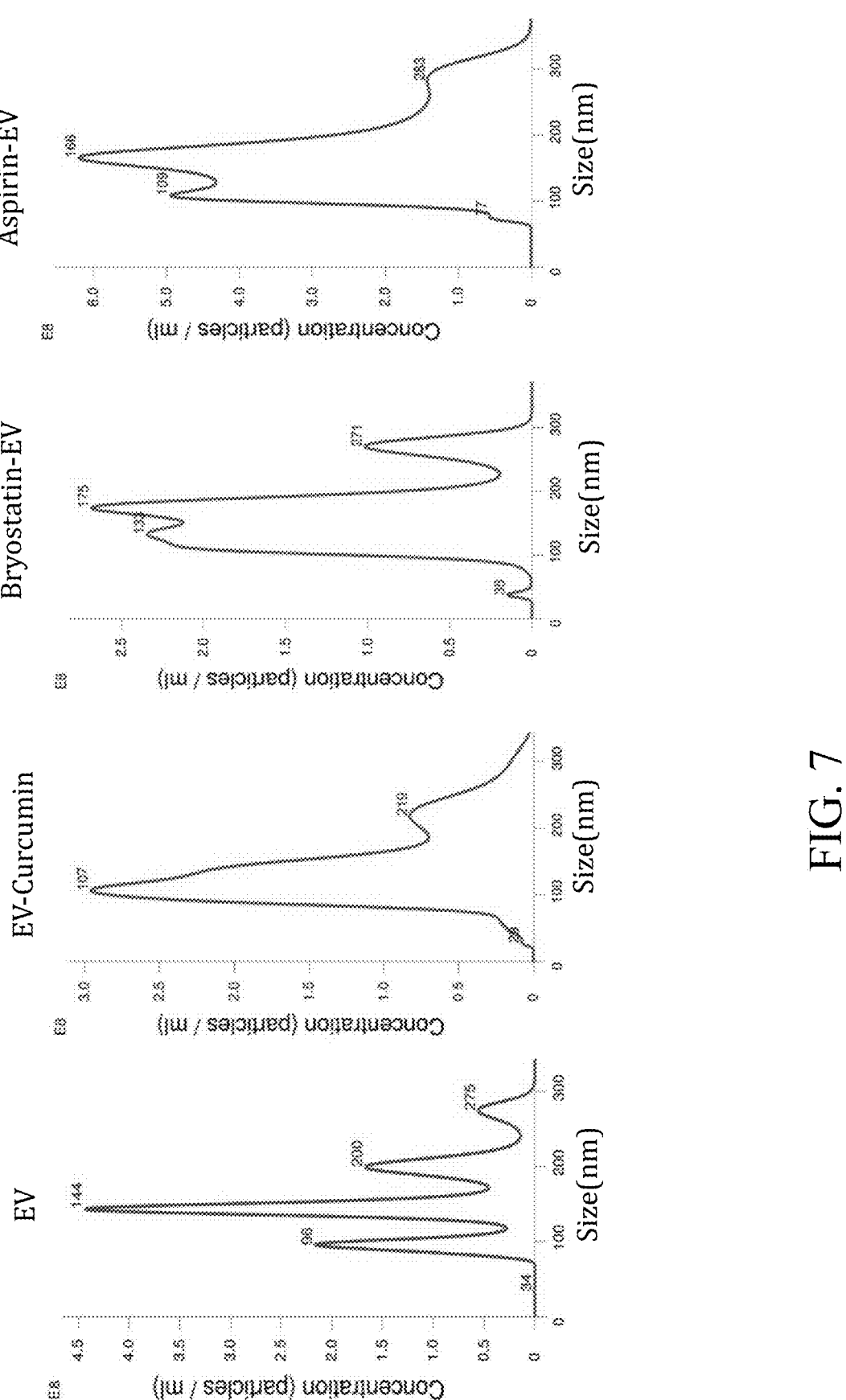
FIG. 7 is the data of EVs tracking analysis that depicts the concentration and size of specified EVs according to Example 2 of the present disclosure. Naïve EVs show a size of mode at 144 nm, EVs incorporating curcumin after isolation (EV-curcumin) reveal a smaller size of mode, EVs derived from pre-culture with bryostatin (bryostatin-EV) show a larger size and EVs derived from preculture with aspirin show a larger size and the highest concentration.

The protein profiles of EVs derived from ucMSCs (i.e., MEV) were dramatically different from that derived from DLD-1 colon cancer cells (i.e., DEV), while the incorporation of curcumin marginally altered the protein expression (FIG. 6). A total of 1160 proteins was identified by iTRAQ (isobaric tag for relative and absolute quantitation) LC/MS-MS spectrometry, in which only the difference at changes >2 fold or <1/2 fold was defined. The protein profiles of specified EVs were summarized in Table 4.

TABLE 4

| Protein profiles of specified EVs | | |
|---|---|---|
| EVs | DEV/MEV | EV-curcumin/MEV |
| >2X Up-expression | 135 | 17 |
| >2X Down-expression | 182 | 34 |
| >4X Up-expression | 25 | 3 |
| >4X Down-expression | 29 | 1 |

The data of Table 4 indicated that when defining the difference at changes >2 fold or <1/2 fold, 317 (135+182) proteins were different between ucMSC-naive EVs (MEV) and EVs derived from DLD-1 cancer cells (DEV), and 51 (17+34) proteins are different between MEV and ucMSC-naive EVs with curcumin incorporation (EV-curcumin). When defining the difference at changes >4 fold or <1/4 fold, 54 (25+29) proteins were different between ucMSC-naive EVs (MEV) and EVs derived from DLD-1 cancer cells (DEV), and only 4 proteins (increases in 3: Ras-related protein Rab-1A, Receptor-type tyrosine-protein phosphatase F, Cell adhesion molecule 1; decrease in one: Hepatoma-derived growth factor) were different between MEV and MEV with curcumin incorporation (EV-curcumin) (Table 3). These changes could be implicated in anti-tumor or anti-inflammation treatment.

Figure 9:
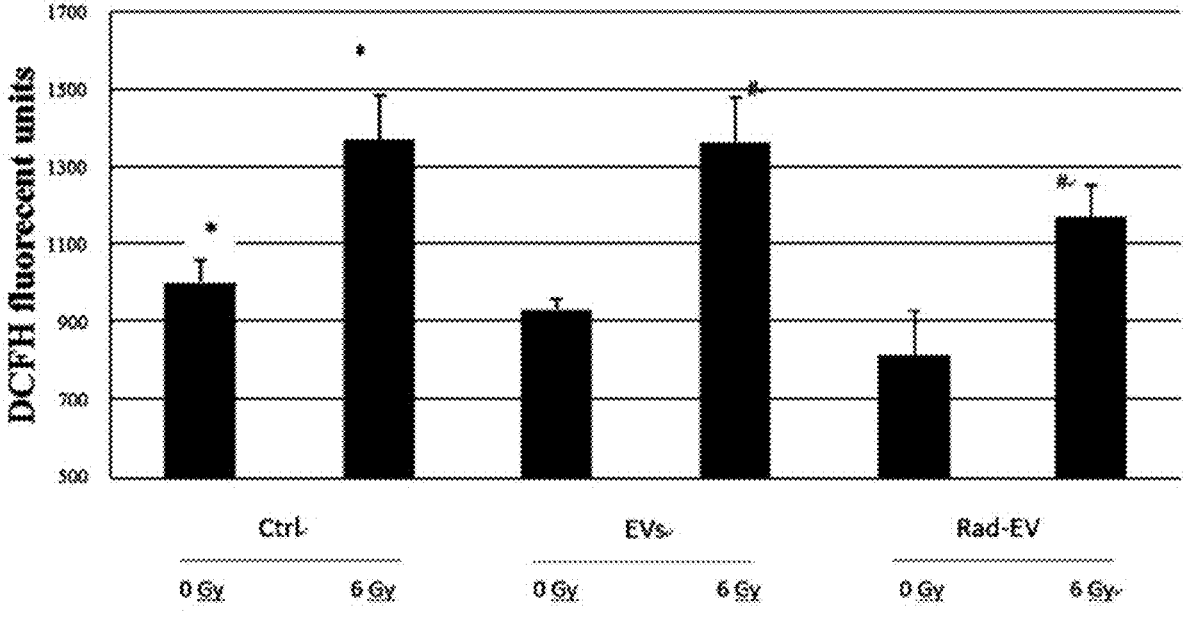
FIG. 9 is a histogram depicting the protecting effect of EVs on irradiation-induced reactive oxygen species (ROS) production according to Example 4 of the present disclosure, in which the EVs were ucMSC-irradiation-EV (i.e., the EVs isolated from ucMSCs irradiated with or without 3 Gy (sublethal dose) delivered by a linear accelerator in a single fraction). Ctrl: the ucMSCs treated with PBS and irradiated with 0 or 6 Gy of X-ray; EVs: the ucMSCs treated with ucMSCs-naive-EVs and irradiated with 0 or 6 Gy of X-ray; Rad-EV: the ucMSCs treated with ucMSC-irradiation-EV and irradiated with 0 or 6 Gy of X-ray. The P values are calculated by Mann Whitney U test. * denotes P<0.05 between 0 Gy irradiation and 6 Gy irradiation of Ctrl group. # denotes P<0.05 between 6 Gy irradiation of EVs group and 6 Gy irradiation of Rad-EV group.

Example 4 ucMSC-Irradiation-EVs Reduced Reactive Oxygen Species (ROS) by ucMSCs Higher dose of irradiation (6 Gy) significantly increased the level of ROS in ucMSCs (FIG. 9). The data of FIG. 9 further indicated that the ucMSC-irradiation-EVs harvested from the precondition of 3 Gy irradiation (Rad-EVs) significantly reduced the ROS production in ucMSCs exposed to a higher dose of irradiation at 6 Gy in four reproducible experiments; in contrast, the ucMSC-naive-EVs (EVs) harvested without preconditional irradiation did not exhibit the protecting effect.

Example 5 EV-ZIP Modulated T Cell Differentiation

Figure 10:
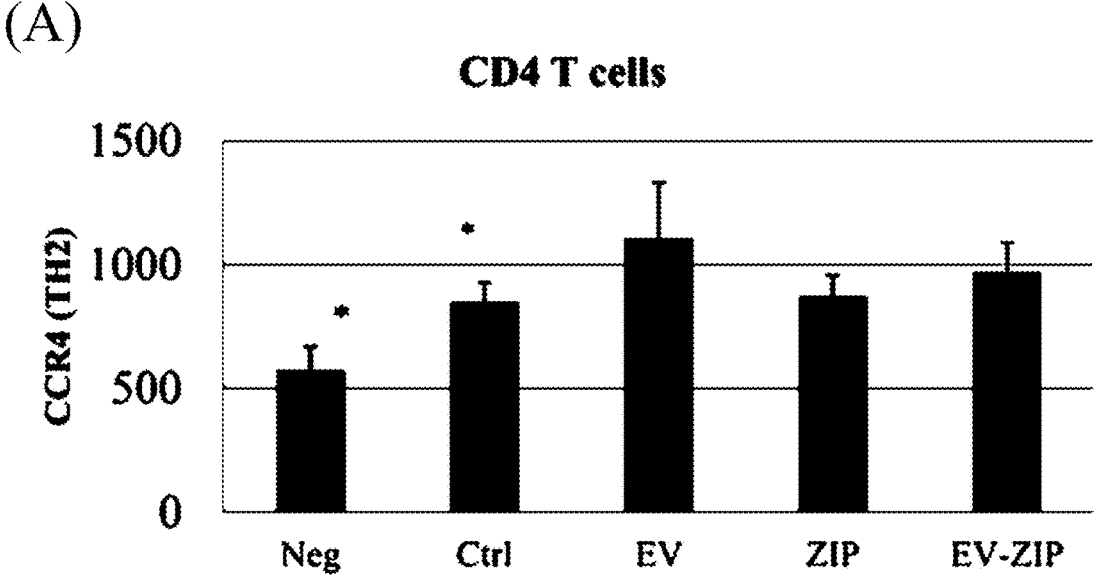
FIG. 10 is the data depicting the effect of specified treatment on T cell differentiation according to Example 5 of the present disclosure. Panel A: the expression of CCR4 on $CD4^+$ T cells; * denotes P<0.05 between Neg group and Ctrl group. Panel B: the expression of CCR4 on $CD8^+$ T cells; * denotes P<0.05 between Ctrl group and EV group; # denotes P<0.05 between EV group and EV-ZIP group. Neg: PBS treatment only; Ctrl: the treatment of anti-CD3 and anti-CD28 antibodies; EV: the treatment of anti-CD3 and anti-CD28 antibodies in the presence of ucMSC-naive-EV; ZIP: the treatment of polypeptide of SEQ ID NO: 1; EV-ZIP: the treatment of EV-ZIP.
Figure 10:
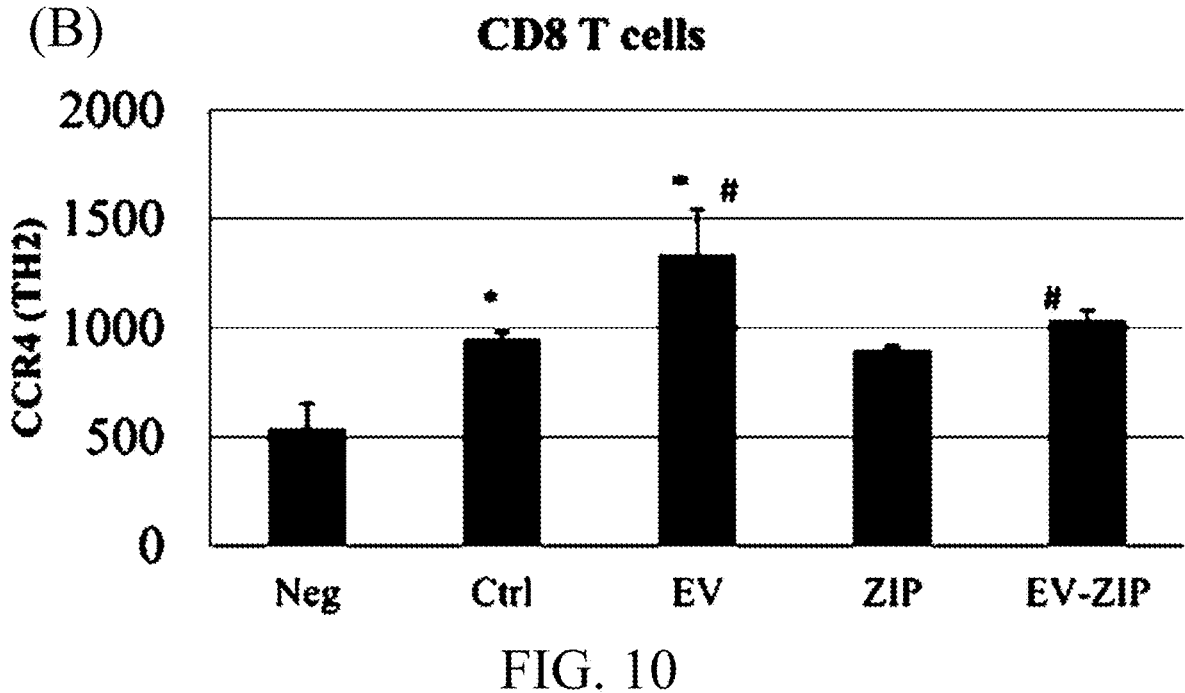

Resting T ($CD4^+$ and $CD8^+$ T cells) cells had low CCR4 expressed thereon (Neg group), and the stimulation of anti-CD3 (10 ug/ml) and anti-CD28 (2 ug/ml) for 4 days as a positive control (Ctrl group) induced significant increases in CCR4 expression on CD8 and CD4 cells ($P<0.05$, n=4) (FIG. 10). Additional administration of EVs with or without polypeptide incorporation on day 2 and day 3 showed varied effects on the Th2 cell differentiation, in which the treatment of ucMSC-EVs (EV) significantly enhanced CCR4 expression (* denotes $P<0.05$, n=4), and EV-ZIP (EV-ZIP) significantly suppressed the CCR4 expression on CD8 but not on CD4 cells (# denotes $P<0.05$, n=4) (FIG. 10).

Figure 11:
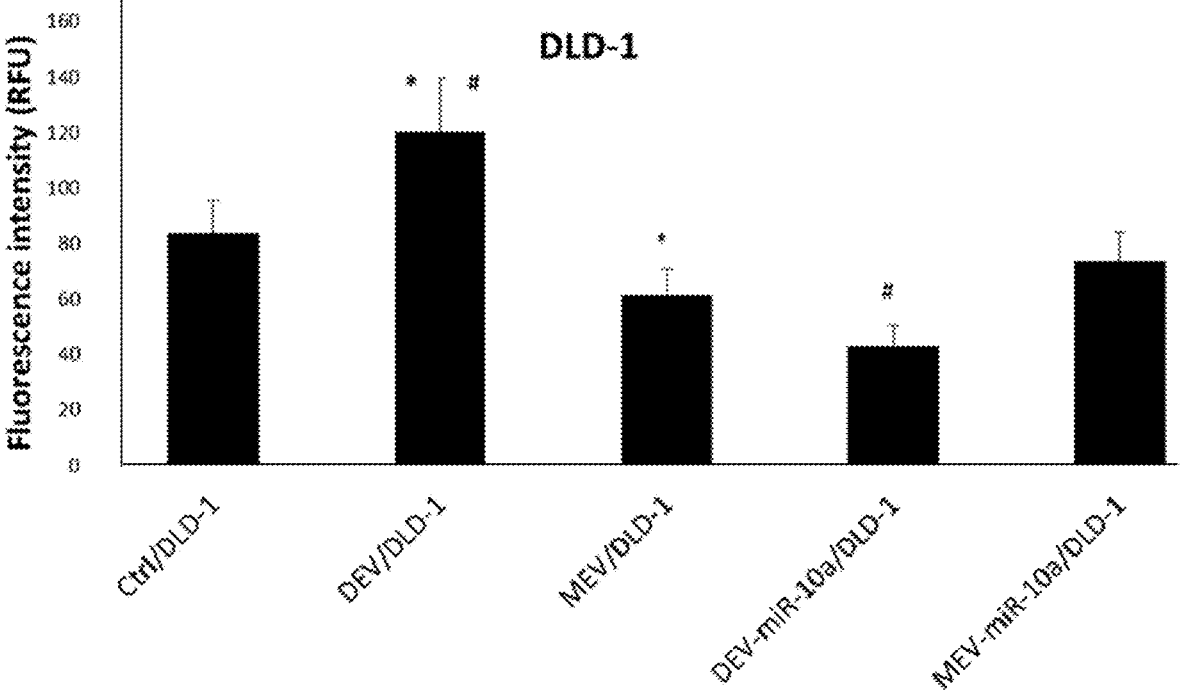
FIG. 11 is a histogram depicting the anti-migration effect of specified EVs on cancer cells according to Example 6 of the present disclosure. Ctrl/DLD-1: the DLD-1 cells treated with PBS; DEV/DLD-1: the DLD-1 cells treated with DLD-1-derived EVs; MEV/DLD-1: the DLD-1 cells treated with ucMSC-naive-EV; DEV-miR-10a/DLD-1: the DLD-1 cells treated with EVs, which was derived from DLD-1 cells and comprised miRNA10a therein; MEV-miR-10a/DLD-1: the DLD-1 cells treated with EV-miRNA10a. * denotes by P<0.05 between DEV/DLD-1 group and MEV/DLD-1 group. # denotes by P<0.05 between DEV/DLD-1 group and DEV-miR-10a/DLD-1 group.

Example 6 EV-miRNA10a Modulated Cancer Cell Migration ucMSC-naive-EVs carry its own specific miRNA profiles (FIG. 5), but not carry all human cell miRNAs. For those under-expression or over-expression of miRNAs in EVs, the antagomir for combating the expression of over-expressed miRNAs or the agomir for enhancing the expression of under-expressed miRNAs may be incorporated in EVs so as to improve the bio-functions of EVs. In this example, the antagomir of miRNA10a was incorporated into EVs, and the anti-tumor effect thereof was evaluated. The data of FIG. 11 demonstrated that the EVs isolated from DLD-1 cancer cells (DEV) enhanced DLD-1 cell migration, and the treatment of ucMSC-naive-EV (MEV) significantly suppressed DLD-1 cell migration. Compared with DEV, the incorporation of miRNA10a significantly suppressed DLD-1 cell migration (FIG. 11).

Example 7 Therapeutic Effect in Animal Study

7.1 Skin Topical Application of EVs for Skin Psoriasis Disease

To evaluate the therapeutic effect of the present EV formulation on skin psoriasis disease, imiquimod was used to induce psoriasis in a mouse model followed by the treatment of specified EVs in accordance with the protocol illustrated in Materials and Methods. The data was depicted in FIG. 12.

Figure 12:
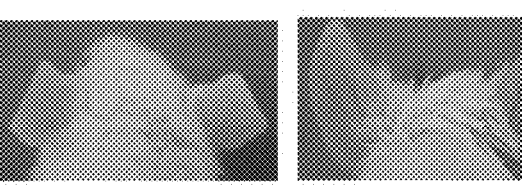
FIG. 12 is the data depicting the therapeutic effect of specified treatment on psoriasis in a mouse model according to Example 7 of the present disclosure. Panels A and B are respectively the photographs and quantified data of ear auricle thickness. Control: the mice treated with PBS only; Vehicle: the mice administrated with imiquimod followed by the treatment of PBS; EV: the mice administrated with imiquimod followed by the treatment of ucMSC-naive-EV; EV-curcumin: the mice administrated with imiquimod followed by the treatment of EV-curcumin. * denotes P<0.05 as tested by Mann Whitney U test; compared with the control group.
Figure 12:
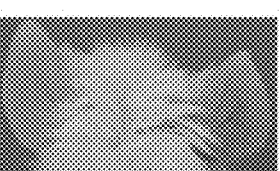
Figure 12:
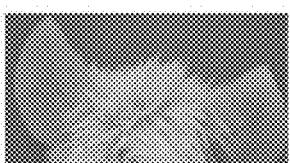
Figure 12:
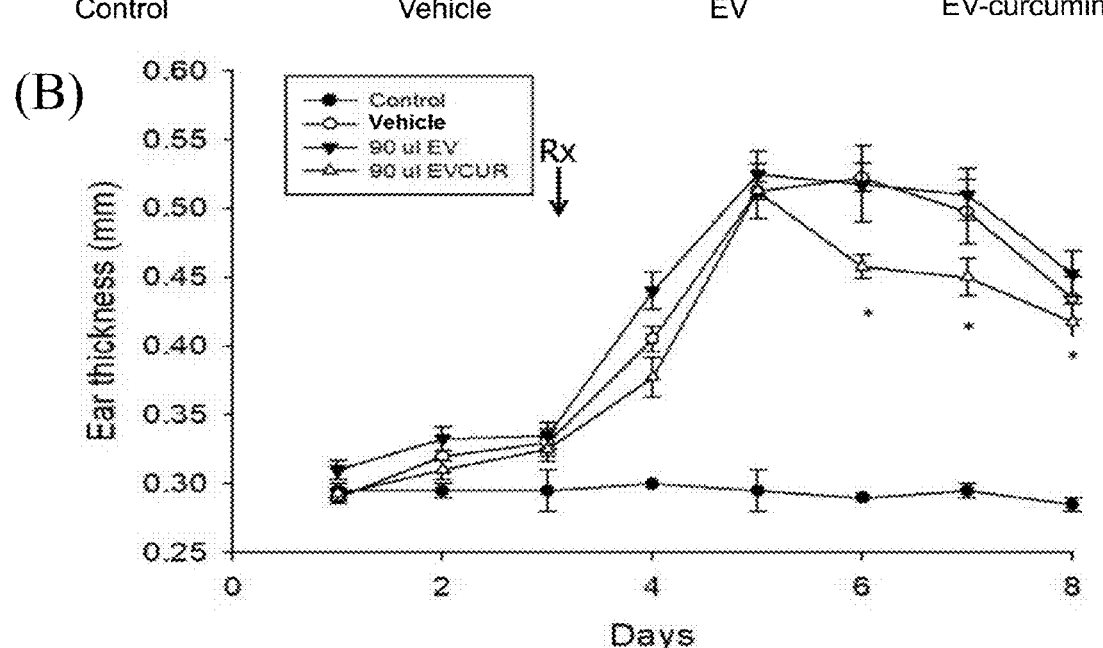

As shown in FIG. 12 (Panel A), a set of experiments with representative photo pictures showed the induction of skin psoriasis-like lesions and effective treatment responses. The quantified result indicated that administrating imiquimod (Vehicle) obviously increased ear thickness of mice, while the treatment of EV-curcumin significantly reduced the psoriasis scores (ear auricle thickness) (FIG. 12, Panel B).

7.2 Mucosal Application of EVs for Dry Eye Disease

The effect of the present EV formulation on the treatment of dry eye disease as investigated in this example. The BALB/c mice were treated in accordance with the protocol illustrated in Materials and Methods. The improvement of dry eyes is assessed by changes of the fluorescein deposition scores under fluoromicroscopy, and the result was depicted in FIG. 13.

Figure 13:
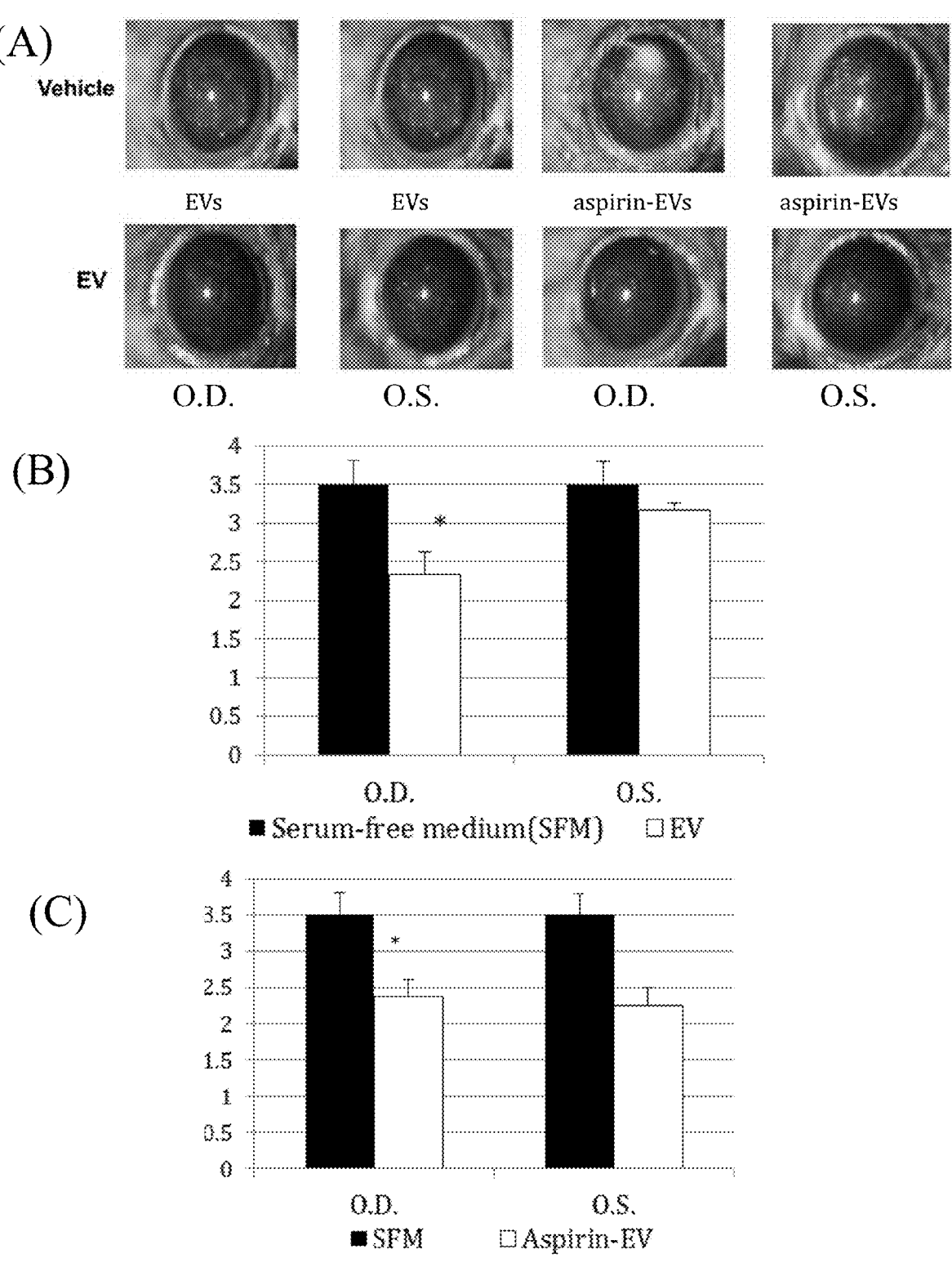
FIG. 13 is data depicting the therapeutic effect of specified treatment on dry eye in a mouse model according to Example 7 of the present disclosure. Panel A: photographs depicting the conjunctiva of mice received vehicle or specified treatment. Panel B: the dry eye score of mice treated with serum-free medium (SFM) or ucMSC-naive-EV (EV). Panel C: the dry eye score of mice treated with serum-free medium (SFM) or aspirin-EV. O.D.: right eye; O.S.: left eye. * denotes P<0.05 as analyzed by Mann Whitney U test; compared with SFM group.

The photographs showed the responses of representative treatments (FIG. 13, Panel A). The quantified results depicted that compared with medium only (SFM, serving as the negative control), the treatment of ucMSC-naive-EVs (EV) or aspirin-EV (Asp-EV) significantly reduced the dry eye scores (FIG. 13, Panels B and C).

7.3 Parenteral Administration of EVs to Treat Hearing Loss

The therapeutic effect of the present EV formulation on hearing loss was examined in this example. The C57BL/6 mice were treated in accordance with the protocol illustrated in Materials and Methods, and the data was depicted in FIG. 14. To obtain the ucMSC-EVs preparations with and without curcumin incorporation enough for the animal study requiring a larger amount of EVs for daily intraperitoneal injection, batches of ucMSC-EVs were prepared in paired formulations with and without curcumin incorporation, and stored the paired formulations at −80° C. for at least 3 months. To make sure homogeneous application of ucMSC-EV to each mouse, different batches of EVs were thawed and mixed for the experiment right before the animal study. This suggests that the EVs formulations were stable in frozen storage without anti-freezer.

Figure 14:
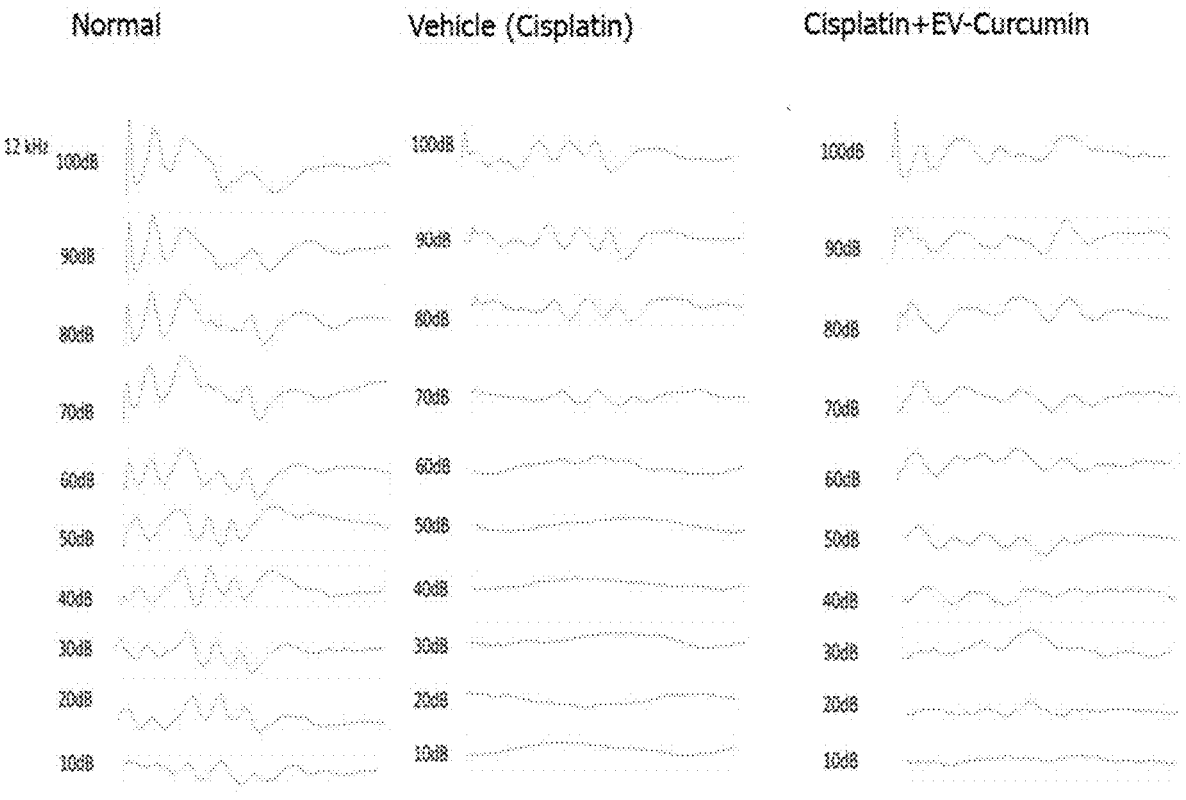
FIG. 14 is data depicting the protecting effect of specified treatment on hearing loss in a mouse model according to Example 7 of the present disclosure. Panels A and B: the auditory brain response (ABR) results of mice receiving specified treatment. Panel C: the immunofluorescence images of organ of Corti explants, in which arrows indicated the loss of hair cells after treatment. Scale bar represents 50 μm. Vehicle: the mice administrated with cisplatin followed by the treatment of PBS; EV: the mice administrated with cisplatin followed by the treatment of ucMSC-naive-EV; EV-curcumin: the mice administrated with cisplatin followed by the treatment of EV-curcumin; curcumin: the mice administrated with cisplatin followed by the treatment of curcumin.
Figure 14:
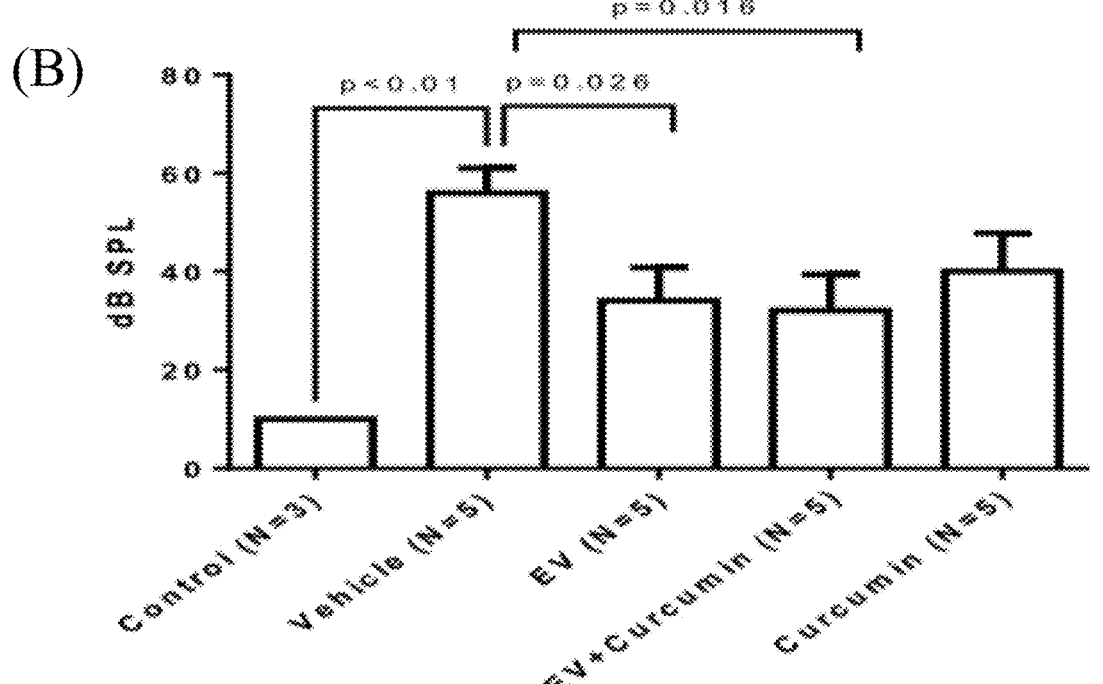
Figure 14:
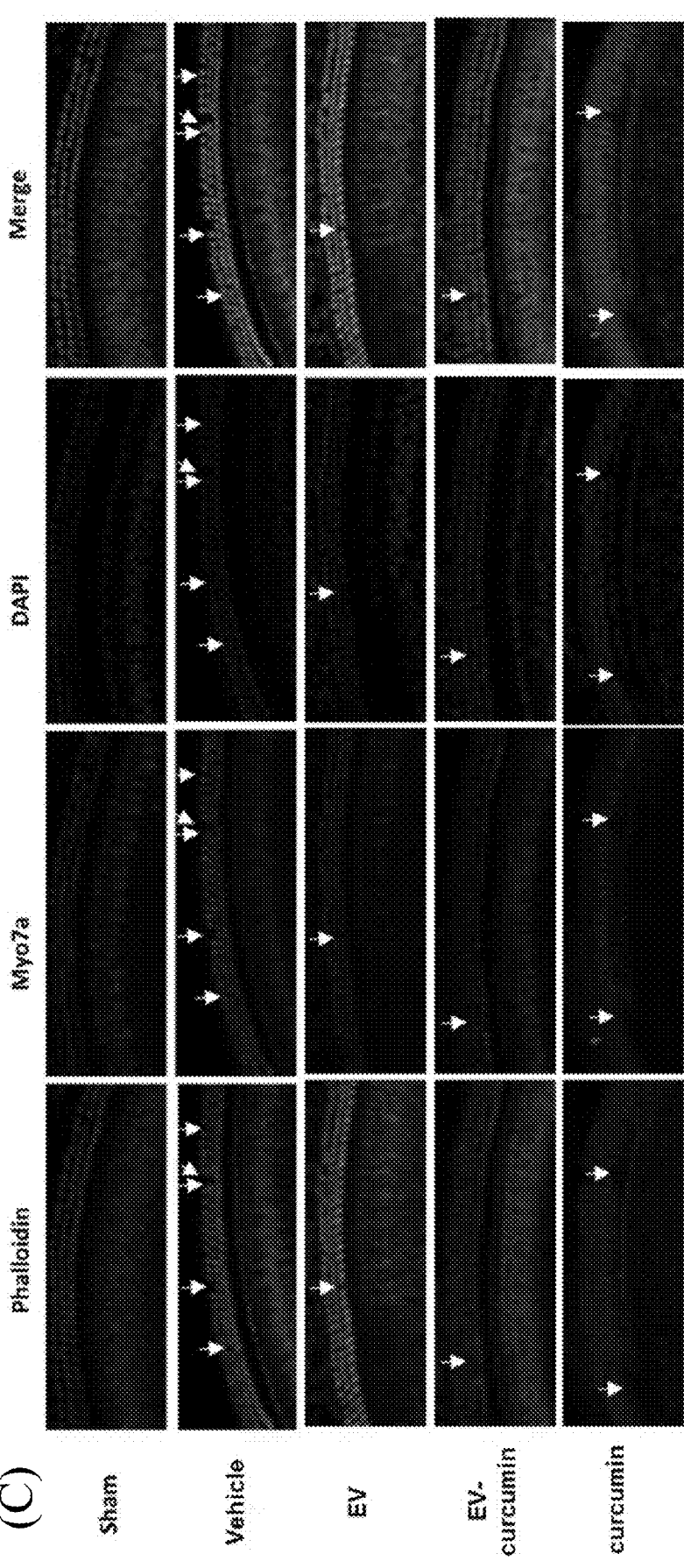

The administration of cisplatin (Vehicle) induced hearing loss in mice, and the treatment of ucMSC-naive-EVs (EV) and EV-curcumin, but not curcumin alone, significantly rescued the cisplatin-induced hearing loss (FIG. 14, Panels A and B). The inner ear cells were stained with phalloidin (green), myosin7a (MYO7A, red) and nucleus (DAPI, blue), and the data demonstrated that compared with control group (Cisplatin), the treatment of ucMSC-naive-EVs (EV) or EV-curcumin obviously reduced the level of cells death caused by cisplatin (FIG. 14, Panel C).

7.4 Intraperitoneal Application of EVs for Anti-Aging Effect

Whether the present EV formulation exhibited an anti-aging effect in animals was investigated in this example. The mice were treated in accordance with the protocol illustrated in Materials and Methods, and the data was depicted in FIG. 15.

Figure 15:
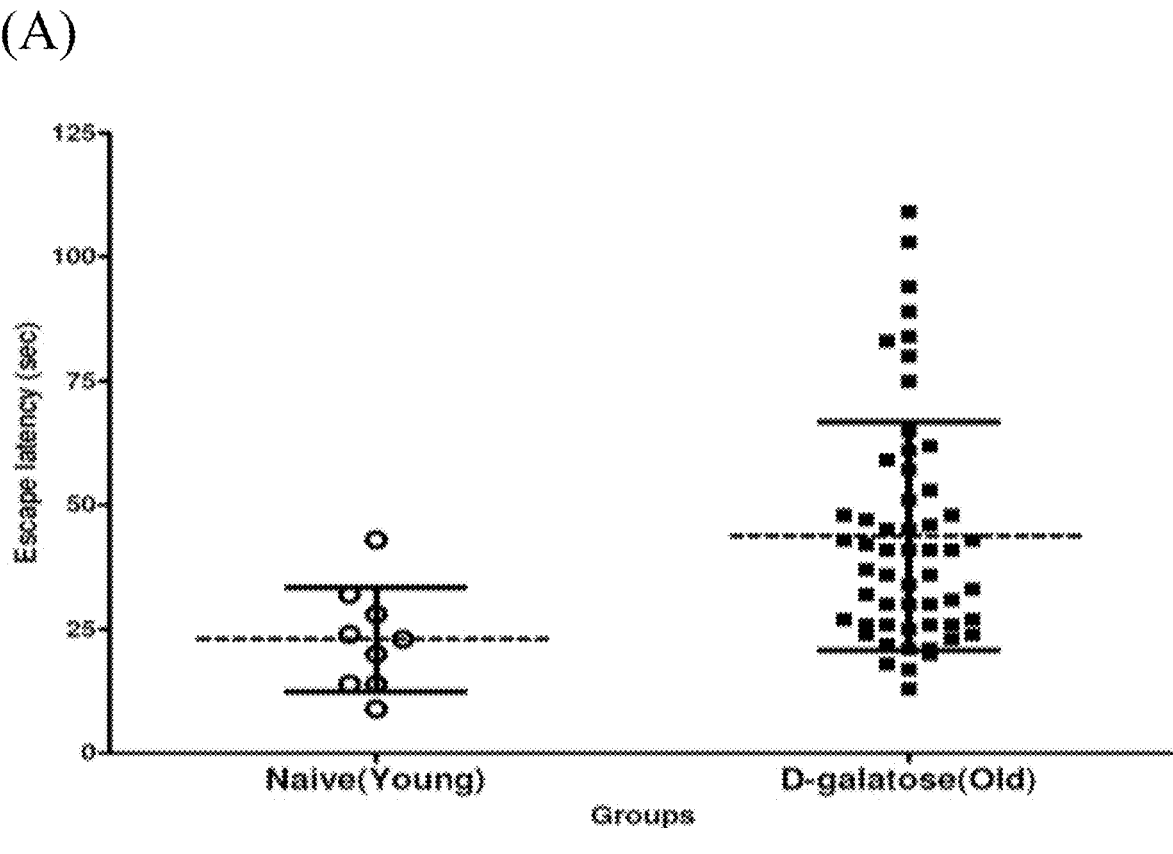
FIG. 15 is the data depicting the anti-aging effect of specified treatment in a mouse model according to Example 7 of the present disclosure. Panel A: Escape latency of mice administered with or without D-galactose. Panel B: Escape latency of mice receiving specified treatments.
Figure 15:
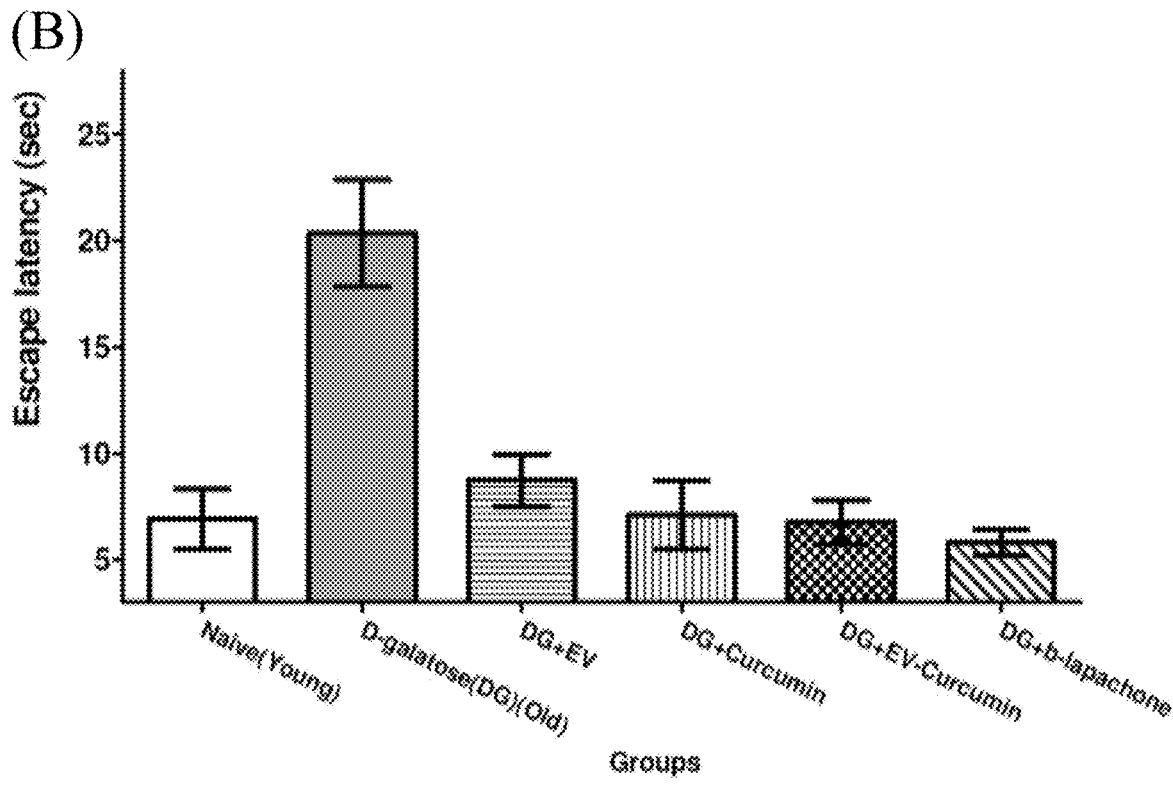

The data of Morris water maze demonstrated that the administration of D-galactose-induced cognition impairment. Specifically, compared with the naive mice, the mice receiving D-galactose for 6 weeks took a significantly longer time to reach a safety island in the water pool (FIG. 15, Panel A). The treatment of ucMSC-naive-EVs (DG+EV), Curcumin (DG+Curcumin), EV-Curcumin (DG+EV-curcumin) or β-lapachone (DG+β-lapachone) obviously reduced the time to reach the safety island (FIG. 15, Panel B).

7.5 Distribution of EVs in Spinal Cord

For the purpose of evaluating the use of the present EV formulation in the treatment of spinal cord injury, the ucMSC-naive-EVs were labeled with CFSE followed by intrathecally injected into mice as described in Materials and Methods.

Figure 16:
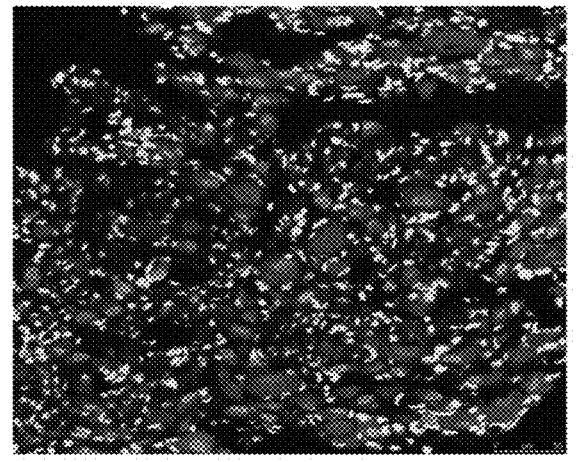
FIG. 16 is the data depicting the distribution of ucMSC-naive-EV in the spinal cord according to Example 7 of the present disclosure.
Figure 16:
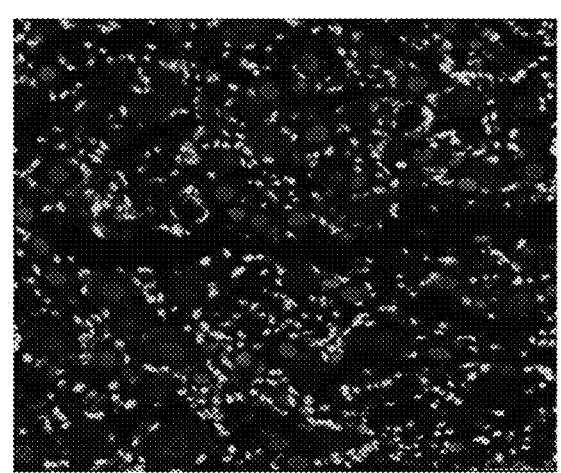

As the data of FIG. 16 depicted, the CFSE-labeled EVs were found in the L5 injured dorsal root ganglion but not in the uninjured L4 dorsal root ganglion. The data shown are one set of the representative experiment with 3 reproducible experiments. The data suggested that the ucMSC-naive-EVs specifically entered the injured (inflammatory) tissue but not normal tissue.

Taken together, these results demonstrated that the present EV formulation is useful in treating various diseases and/or conditions, including cancers, psoriasis, dry eye, hearing loss, aging, and spinal cord injury.

In conclusion, the present disclosure provides an EV formulation for treating diseases. The present EV formulation comprises an ucMSC-derived EV, and one or more active agents (e.g., growth factor, siRNA, polypeptide, small molecule, plant extract, or the combination thereof) encapsulated in the liposome structure of the ucMSC-derived EV via pre-conditional treatment or post-isolation incorporation. According to examples of the present disclosure, the present EV formulation is prepared between pH=6-10 condition, and could be stably stored under −80° temperature without the addition of anti-freezer. The active agent(s) may additively or synergistically enhance the therapeutic effect of the ucMSC-derived EVs, and thus, providing a more efficient means to treat diseases.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

---

What is claimed is:

1. A method of treating an inflammatory disease in a subject, comprising administering to the subject an effective amount of a formulation comprising an extracellular vesicle (EV) derived from a mesenchymal stem cell and curcumin encapsulated in the EV, wherein the mesenchymal stem cell is isolated from Wharton jelly of umbilical cord and is CD29$^+$, CD34$^-$, CD44$^+$ and CD73$^+$, wherein the inflammatory disease is psoriasis, and wherein the formulation is prepared by:

(a) culturing the mesenchymal stem cell in the presence of aspirin;

(b) culturing the mesenchymal stem cell obtained in step (a) under 1% to 5% $O_2$ and in serum free medium;

(c) isolating the EV from the cultured mesenchymal stem cell obtained in step (b); and (d) incubating the isolated EV obtained in step (c) with curcumin under a condition of pH 6.0 to 10.0 to encapsulate the curcumin in the isolated EV obtained in step (c).

2. The method of claim 1, wherein the formulation is administered to the subject via a route selected from the group consisting of topical, intraconjunctival, intranasal, intratracheal, oral, intraspinal, intravenous, intraarterial, intramuscular, subcutaneous, intraarticular, intraventrical, intracerebroventricular, intraperitoneal injection and intra-middle ear administration.

3. The method of claim 1, wherein the subject is a human.

* * * * *